US012669474B2

(12) United States Patent
    Oshita

(10) Patent No.: US 12,669,474 B2
(45) Date of Patent: Jun. 30, 2026

(54) ODOR MEASURING DEVICE AND ODOR MEASURING METHOD

(71) Applicant: TAIYO YUDEN CO., LTD., Tokyo (JP)

(72) Inventor: Junji Oshita, Tokyo (JP)

(73) Assignee: Taiyo Yuden Co., Ltd., Tokyo (JP)

( * ) Notice: Subject to any disclaimer, the term of this patent is extended or adjusted under 35 U.S.C. 154(b) by 300 days.

(21) Appl. No.: 18/598,421

(22) Filed: Mar. 7, 2024

(65) Prior Publication Data

US 2024/0210355 A1    Jun. 27, 2024

Related U.S. Application Data

(63) Continuation of application No. PCT/JP2022/029585, filed on Aug. 2, 2022.

(30) Foreign Application Priority Data

Sep. 14, 2021    (JP) ................................. 2021-149125

(51) Int. Cl.
    *G01N 29/02*        (2006.01)
    *G01N 33/00*        (2006.01)
(52) U.S. Cl.
    CPC ....... *G01N 29/022* (2013.01); *G01N 33/0027* (2013.01); *G01N 2291/021* (2013.01)
(58) Field of Classification Search
    None
    See application file for complete search history.

(56) References Cited

U.S. PATENT DOCUMENTS

| | | | | |
|---|---|---|---|---|
| 10,365,208 B2 * | 7/2019 | Kolb | ..................... | G01N 29/022 |
| 11,754,492 B2 * | 9/2023 | Uehlinger | .......... | G01N 21/1702 |
| | | | | 73/24.01 |
| 12,111,249 B2 * | 10/2024 | Dehé | ................... | G01N 29/2425 |
| 12,332,161 B2 * | 6/2025 | Zhang | .................... | G01N 21/01 |
| 2021/0033590 A1 | 2/2021 | Hanko et al. | | |
| 2023/0324344 A1 * | 10/2023 | Oshita | ...................... | G01N 5/02 |

FOREIGN PATENT DOCUMENTS

| | | |
|---|---|---|
| JP | 10-19862 | 1/1998 |
| JP | 10-111224 | 4/1998 |
| JP | 11-83820 | 3/1999 |
| JP | 2002-350299 | 12/2002 |

(Continued)

OTHER PUBLICATIONS

International Search Report and Written Opinion cited in PCT Application No. PCT/JP2022/029585, mailed Oct. 25, 2022.

*Primary Examiner* — Suman K Nath
(74) *Attorney, Agent, or Firm* — CHIP LAW GROUP

(57) ABSTRACT

An odor measuring device includes a sensor chamber that stores a sensor detecting an odor substance and has a first inlet and a first outlet, a treatment chamber that stores a measurement object and has a second inlet and a second outlet, a first flow path that connects the first outlet and the second inlet, a second flow path that connects the second outlet and the first inlet, a supplier that circulates a gas between the sensor chamber and the treatment chamber through the first flow path and the second flow path, and a measurer that acquires a detected value from the sensor and measures an odor based on the detected value.

15 Claims, 26 Drawing Sheets

(56)          References Cited

FOREIGN PATENT DOCUMENTS

| JP | 2006-64554  | 3/2006  |
|----|-------------|---------|
| JP | 2016-186426 | 10/2016 |
| JP | 2020-12732  | 1/2020  |
| WO | 2022085345  | 4/2022  |
| WO | 2022137438  | 6/2022  |

* cited by examiner

ODOR MEASURING DEVICE AND ODOR MEASURING METHOD

CROSS-REFERENCE TO RELATED APPLICATION

This application is a continuation application of International Application PCT/JP2022/029585 filed on Aug. 2, 2022 and designated the U.S., which claims the benefits of priorities of Japanese Patent Application No. 2021-149125 filed on Sep. 14, 2021, the entire contents of which are incorporated herein by reference.

FIELD

A certain aspect of the present disclosure relates to an odor measuring device for measuring an odor and an odor measuring method.

BACKGROUND

An odor measuring device using an odor sensor includes a device using a quartz crystal microbalance (QCM). When an odor substance is adsorbed to a sensitive portion of the odor sensor, the electrical characteristic of the odor sensor is changed, and the odor is measured.

For example, Patent Document 1 (Japanese Laid-open Patent Application Publication No. 2002-350299) discloses an odor measuring method in which a predetermined amount of a gas sample is passed through an odor component collecting material, and a dry inert gas is fed to the odor component collecting material at a high speed, whereby the gas sample is separated from the odor component collecting material. In addition, Patent Document 2 (Japanese Laid-open Patent Application Publication No. 10-19862) discloses an odor detecting method in which a sampling gas is passed through an adsorption/desorption portion to adsorb an odor component in the adsorption/desorption portion, and then an odorless gas is passed through the adsorption/desorption portion to sense the odorless gas having the odor component adsorbed thereon.

Furthermore, Patent Document 3 (Japanese Laid-open Patent Application Publication No. 2020-12732) discloses an odor measuring method that detects a direction of gas arrival based on the direction of an intake port, by using a concentration distribution measuring device including a measuring chamber for storing a gas sensor, an intake port connected to the measuring chamber, and an information acquiring portion for acquiring information including the position and direction of the intake port. Furthermore, Patent Document 4 (Japanese Laid-open Patent Application Publication No. 2016-186426) discloses an odor discriminating method for discriminating and detecting an odor using an odor discriminating system. The odor discriminating system includes an odor discriminating element portion that discriminates the odor by a molecular size filter or a polarity filter and is provided between a sample storing chamber and an odor measuring chamber.

SUMMARY OF THE INVENTION

However, in the methods described in Patent Documents 1 to 4, when the odor to be measured has a low concentration, it is not easy to detect the odor due to insufficient sensitivity and the influence of disturbance. In these patent documents, concentrating for detecting a low concentration is described, but a means for stably measuring the odor having the low concentration is not described.

According to a first aspect of the present invention, there is provided an odor measuring device includes a sensor chamber, a treatment chamber, a first flow path, a second flow path, a supplier, and a measurer. The sensor chamber stores a sensor detecting an odor substance and has a first inlet and a first outlet. The treatment chamber stores a measurement object and has a second inlet and a second outlet. The first flow path connects the first outlet and the second inlet. The second flow path connects the second outlet and the first inlet. The supplier circulates a gas between the sensor chamber and the treatment chamber through the first flow path and the second flow path. The measurer acquires a detected value from the sensor and measures an odor based on the detected value.

According to a second aspect of the present invention, there is provided an odor measuring device includes a sensor chamber, a treatment chamber, a flow path, a supplier, and a measurer. The sensor chamber stores a sensor detecting an odor substance and has a first inlet and a first outlet. The treatment chamber that includes a desorption treatment chamber having a second outlet and storing a measurement object, and a gas treatment chamber having a second inlet and communicating with the desorption treatment chamber through an opening. The desorption treatment chamber has a lower surface provided with the opening and an upper surface facing the lower surface, and includes a pressing portion projecting from the upper surface toward the lower surface and pressing the measurement object together with the lower surface. The flow path connects the second outlet and the first inlet. The supplier delivers a gas in the treatment chamber to the sensor chamber through the flow path. The measurer acquires a detected value from the sensor and measures an odor based on the detected value.

According to a third aspect of the present invention, there is provided an odor measuring method is executed by an odor measuring device that includes a sensor chamber that stores a sensor detecting an odor substance and has a first inlet and a first outlet, a treatment chamber that has a second inlet and a second outlet, a first flow path that connects the first outlet and the second inlet, a second flow path that connects the second outlet and the first inlet, and a supplier that circulates a gas between the sensor chamber and the treatment chamber through the first flow path and the second flow path. The odor measuring method includes storing a measurement object in the treatment chamber, circulating the gas between the sensor chamber and the treatment chamber by the supplier, and measuring an odor based on a detected value acquired from the sensor.

DETAILED DESCRIPTION

An odor measuring device according to an embodiment of the present disclosure will be described below with reference to the drawings. In the following description, the term "odor" means an aggregate of a plurality of types of odor substances. Examples of odor substances include molecules such as acetone and toluene. Since the adsorption film of each of the odor sensors described later has selectivity of the odor substance to be adsorbed, different types of odors are adsorbed by the adsorption film of each of the odor sensors. In other words, the adsorption films of the respective odor sensors differ in the compositions and amounts of the plurality of types of odor substances to be adsorbed. In the present embodiment, the amount of each odor substance measured by each odor sensor is comprehensively judged, thereby judging the type of odor which is an aggregate of each odor substance. The types of odors include fruit odors, body odors, burning odors caused by broken power cords, and odors from toxic drugs that are banned by law. The details of the above will be described below.

Figure 1:
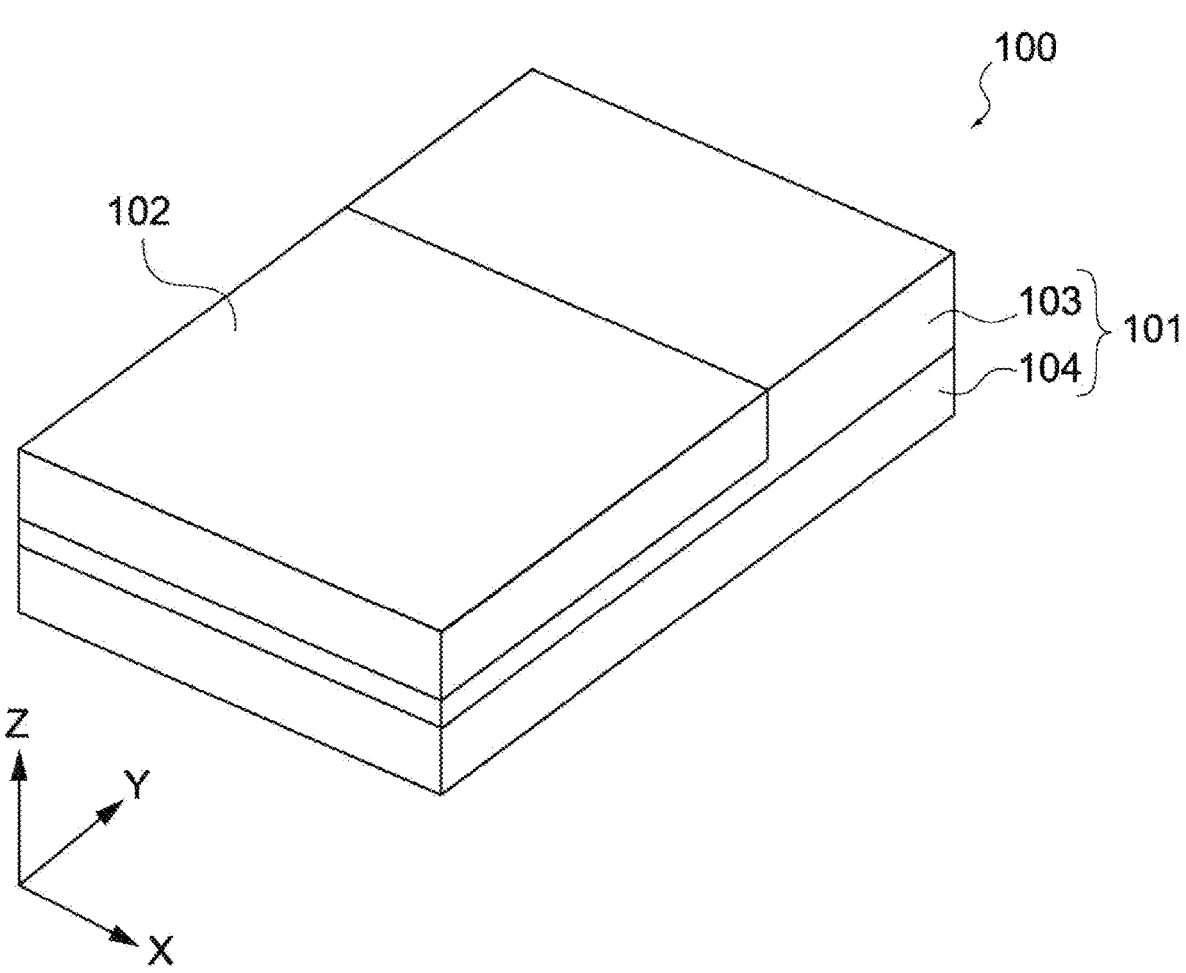
FIG. 1 is a perspective view of an odor measuring device according to an embodiment.
Figure 2:
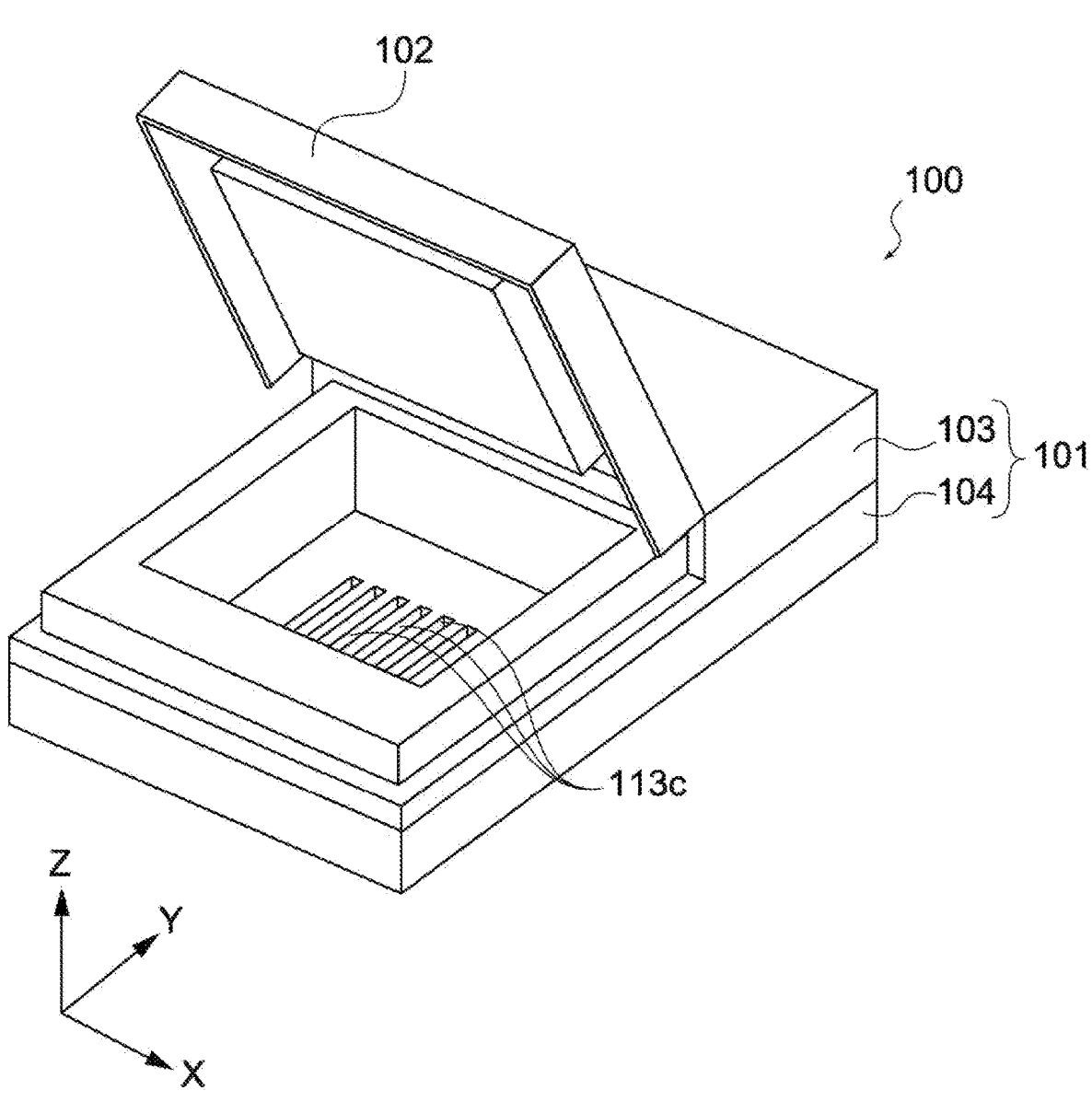
FIG. 2 is a perspective view illustrating a state in which a lid of the odor measuring device is opened.
Figure 3:
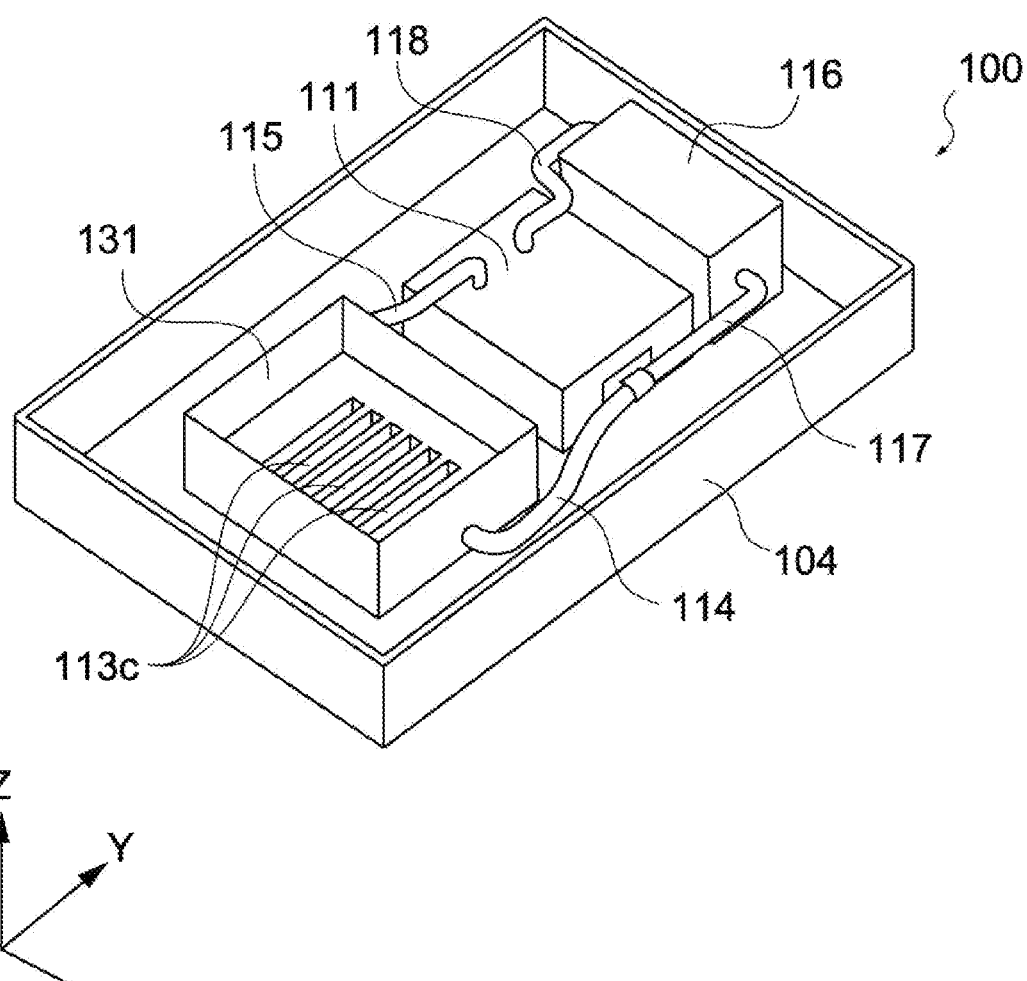
FIG. 3 is a perspective view illustrating the internal structure of the odor measuring device.

FIGS. 1 and 2 are perspective views of an odor measuring device 100 according to the present embodiment, and FIG. 3 is a perspective view of a part of the configuration of the odor measuring device 100. As illustrated in FIGS. 1 and 2, the odor measuring device 100 includes a casing 101 and a lid 102. The casing 101 is formed by joining an upper casing 103 and a lower casing 104. As illustrated in FIG. 2, the lid 102 is openable and closable with respect to the casing 101. The lid 102 is connected to the upper casing 103. The upper casing 103 has a rectangular upper surface, four side surfaces extending downward from the four side edges of the upper surface, and a rectangular lower surface connected to the four side surfaces at a position facing the upper surface. The shape of the upper casing 103 is not limited to such a cube shape, and may be any shape as long as it can store a measurement object described later. An opening is provided in the upper surface for taking in and out the measurement object, and the lid 102 is disposed so as to cover the opening. In FIG. 2, one side of the lid 102 is attached around the opening to allow opening and closing, but the lid 102 may be a cap and may be removable. The upper casing 103 itself may be removable. Then, the lid 102 is opened, and the measurement object is inserted into the lower casing 104.

Figure 4:
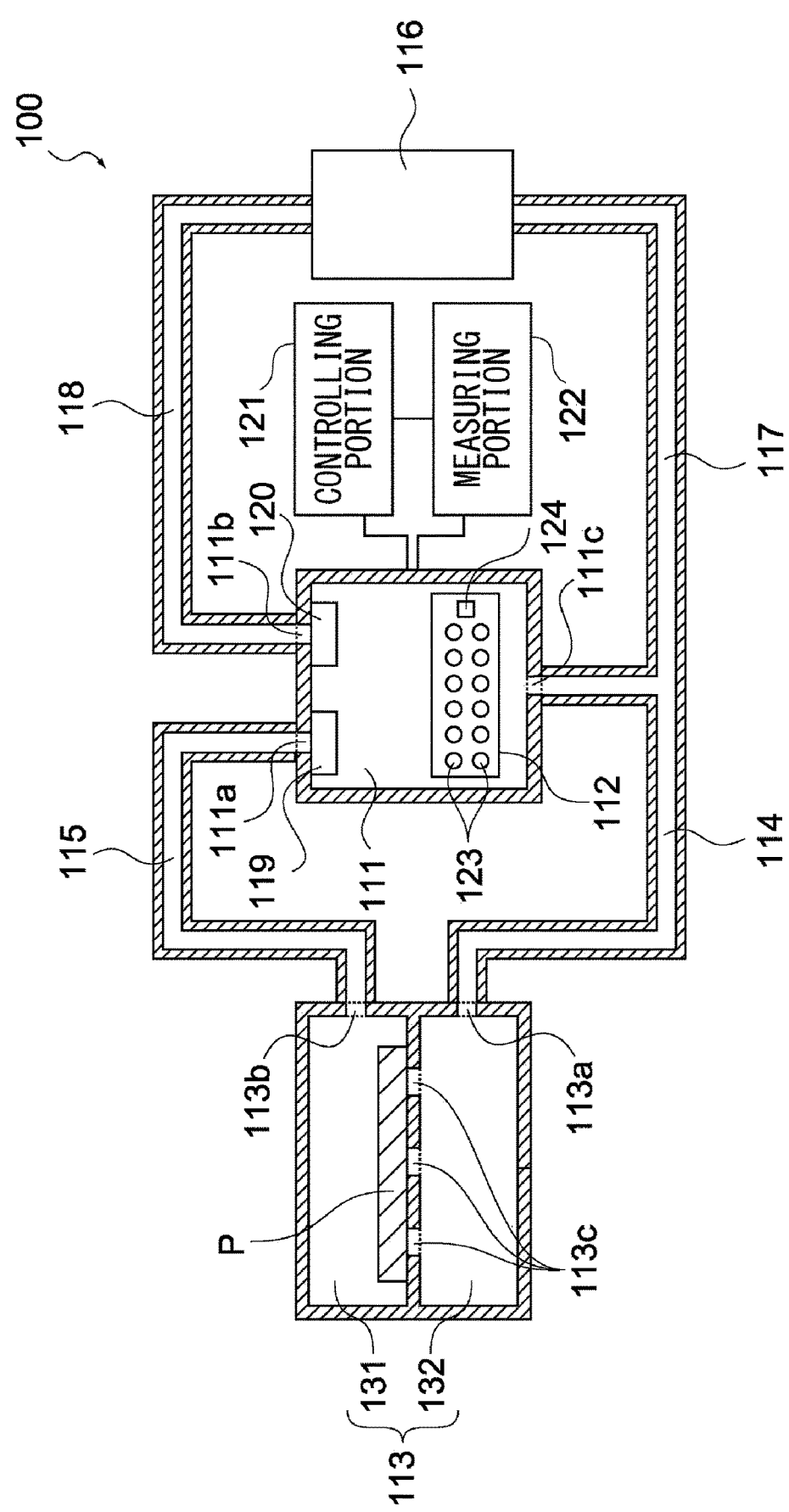
FIG. 4 is a schematic view illustrating the configuration of the odor measuring device.

FIG. 3 is a perspective view of the lower casing 104 in which the upper casing 103 and the lid 102 are not illustrated. FIG. 4 is a schematic view illustrating the configuration of the odor measuring device 100. As illustrated in these figures, the odor measuring device 100 includes a sensor chamber 111, a sensor module 112 installed in the sensor chamber 111, a treatment chamber 113, a first flow path 114, a second flow path 115, a filter 116, a third flow path 117, a fourth flow path 118, a first supplying portion 119, a second supplying portion 120, a controlling portion 121, and a measuring portion 122.

The sensor chamber 111 is a treatment chamber that stores the sensor module 112 and in which a gaseous fluid containing an odor is supplied from the treatment chamber 113 to perform odor detection. As illustrated in FIG. 4, the sensor chamber 111 has a first inlet 111*a*, a third inlet 111*b*, and a first outlet 111*c*. The sensor module 112 includes odor sensors 123 and a humidity sensor 124. The sensor module 112 may further include a temperature sensor. The sensor module 112 preferably includes a plurality of odor sensors 123, and in the present embodiment, 12 odor sensors 123 are provided.

The odor sensor 123 outputs a detected value corresponding to the amount of adsorption of the odor substance. The odor sensor 123 is, for example, a QCM (Quartz Crystal Microbalance) sensor, and includes a vibrator and an adsorption film covering the surface of the vibrator. The vibrator vibrates at a constant resonance frequency when a voltage is applied. The resonance frequency is, for example, 9 MHz. The adsorption film is provided on the vibrator and a specific odor substance is adsorbed. When the odor substance is adsorbed on the adsorption film while the vibrator is vibrated at a predetermined resonance frequency, the weight of the adsorption film increases and the resonance frequency of the vibrator decreases. When the odor substance adsorbed on the adsorption film is desorbed, the weight of the adsorption film decreases, and the resonance frequency of the vibrator increases. The odor sensor 123 outputs a variation amount of the resonance frequency to the measuring portion as a detected value. The odor sensor may be a resistive sensor of polymer or ceramic, a capacitive sensor in which a dielectric is sandwiched between two electrodes and a dielectric constant of the dielectric changes by adsorption, or a vibration sensor such as a film bulk acoustic resonator (FBAR) or surface acoustic wave (SAW), in addition to the QCM of the present embodiment.

The adsorption film is formed of a different material for each odor sensor 123. The odor contained in the gas to be measured includes one or more odor substances. By using different adsorption films for the respective odor sensors 123, a plurality of types of odor substances can be detected. A material used for the adsorption film is appropriately selected according to the type of an odor to be measured. Specifically, as the adsorption film, an organic metal structure (MOF) such as UiO-66, MIL 125, ZIF-8, or the like can be used in addition to cellulose, a fluorine polymer, lecithin, a phthalocyanine compound, a porphyrin compound, polyimide, polypyrrole, polystyrene, an acrylic polymer, sphingomyelin, polybutadiene, polyisoprene, and a polyvinyl alcohol polymer. The adsorption film may include any one of these materials or a combination of two or more of these materials.

The humidity sensor 124 detects the relative humidity of the gas in the sensor chamber 111. As the humidity sensor 124, a known humidity sensor such as a capacitance type sensor in which a capacitance changes in response to moisture, a resistance change type sensor in which an electrical resistance changes in response to moisture, or the like can be used. The humidity sensor 124 may be a sensor in which a hydrophilic adsorption film is formed on one of the odor sensors 123. The humidity sensor 124 outputs the detected relative humidity to the measuring portion. As the temperature sensor, a known temperature sensor such as a thermistor can be used.

Figure 5:
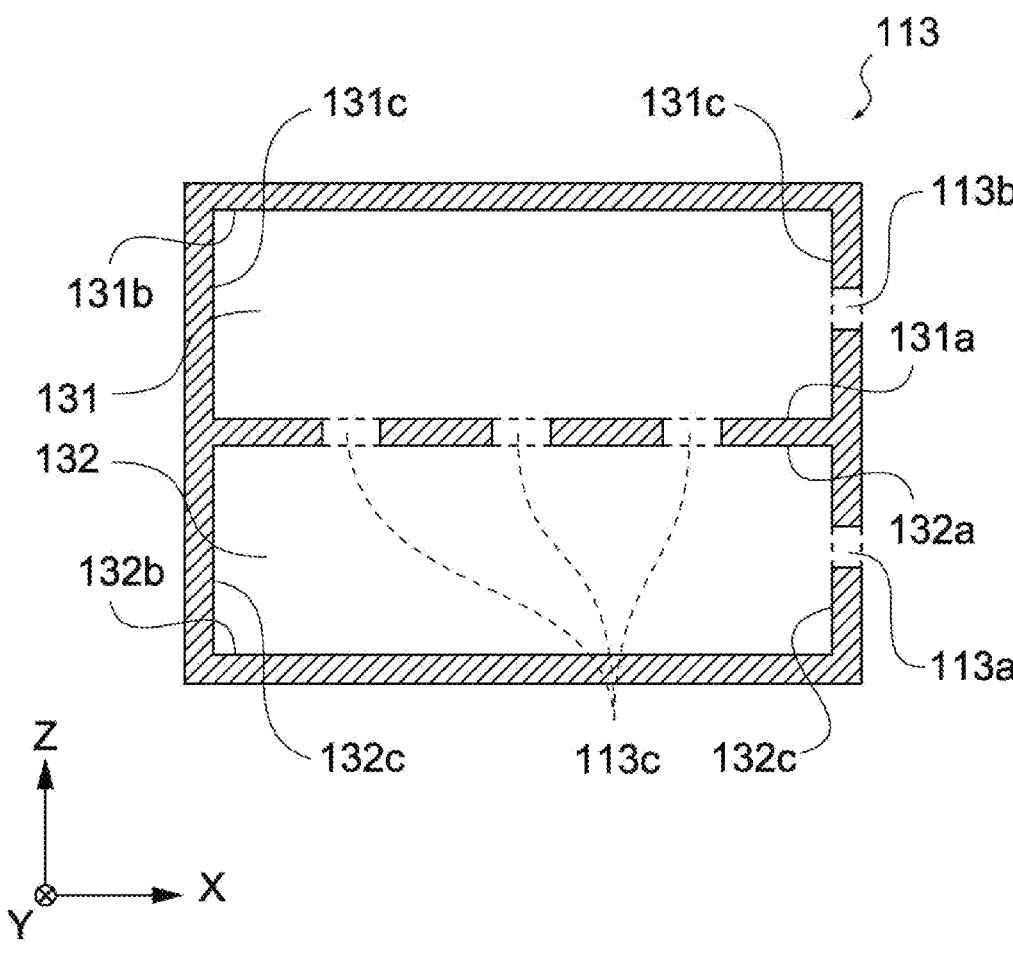
FIG. 5 is a schematic view of a treatment chamber provided in the odor measuring device.

The treatment chamber 113 stores the measurement object and has a second inlet 113a and a second outlet 113b as illustrated in FIG. 4. FIG. 5 is a schematic view illustrating the treatment chamber 113. As illustrated in FIG. 5, the treatment chamber 113 is composed of two chambers, i.e., a desorption treatment chamber 131 and a gas treatment chamber 132. A lower surface 131a of the desorption treatment chamber 131 is shared with an upper surface 132a of the gas treatment chamber 132, the lower surface and the upper surface are integrated as a shared plate, and openings 113c are provided in the shared plate.

Figure 6:
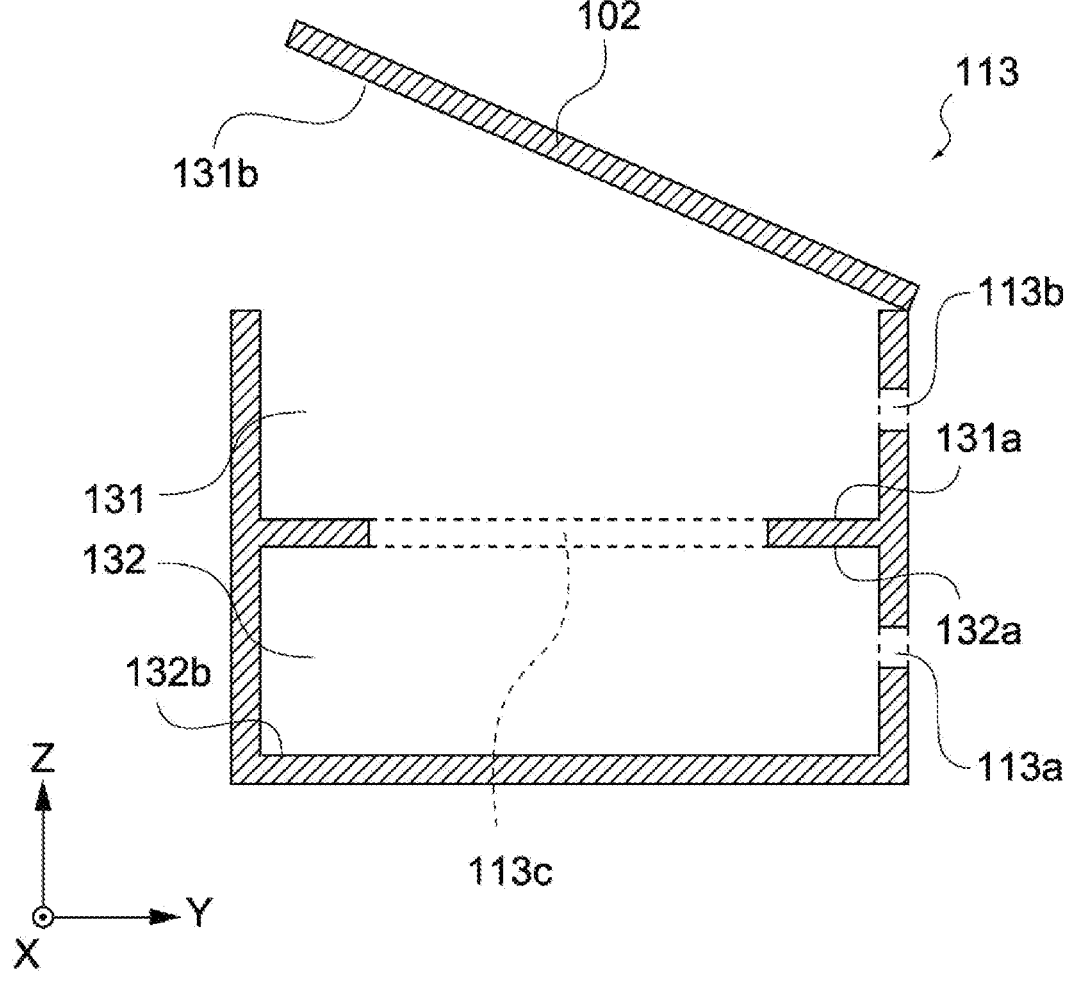
FIG. 6 is a schematic view of an open state of the treatment chamber provided in the odor measuring device.

The desorption treatment chamber 131 is openable and closable. FIG. 6 is a schematic view illustrating opening and closing of the desorption treatment chamber 131. As illustrated in FIGS. 6 and 2, the desorption treatment chamber 131 is opened and closed by the lid 102, and can store the measurement object. In FIG. 4, the measurement object stored in the treatment chamber 113 is illustrated as a measurement object P. The measurement object P is not particularly limited, but is a sheet-like body such as a mask or a cloth. An area around the mouth and the surface of the bag to which the odor substance is adhered are wiped with the cloth, and the cloth is put into the desorption treatment chamber 131. The measurement object P may be an object to which the odor substance is adhered or a source of generation of the odor substance such as a food such as a fruit or a vegetable. The measurement object P is not limited to a solid object, but may be a liquid drink such as juice containing fruit components. In the case of a liquid object, it is desirable to use a pan 161 illustrated in FIG. 23 or to store the liquid object in a container having a hole in the lid so that a volatile gas is released. The desorption treatment chamber 131 has the second outlet 113b. As illustrated in FIG. 5, the desorption treatment chamber 131 has the lower surface 131a, an upper surface 131b, and side surfaces 131c.

The lower surface 131a is a surface on which the measurement object P is placed, and the upper surface 131b is a surface facing the lower surface 131a. The side surfaces 131c connects the lower surface 131a and the upper surface 131b. The upper surface 131b, the lower surface 131a, and the side surfaces 131c constitute a space. The desorption treatment chamber and various components provided in the desorption treatment chamber are collectively referred to as a "desorption treatment device".

The gas treatment chamber 132 is a chamber adjacent to the desorption treatment chamber 131. The gas treatment chamber 132 has the second inlet 113a. As illustrated in FIG. 5, the desorption treatment chamber 131 has the upper surface 132a, a lower surface 132b, and side surfaces 132c. The upper surface 132a is a surface on the back side of the lower surface 131a of the desorption treatment chamber 131, and the lower surface 132b is a surface facing the upper surface 132a. The side surface 132c connects the lower surface 132b and the upper surface 132a. The upper surface 132a, the lower surface 132b, and the side surface 132c constitute a space.

The openings 113c are provided between the lower surface 131a of the desorption treatment chamber 131 and the upper surface 132a of the gas treatment chamber 132. The desorption treatment chamber 131 and the gas treatment chamber 132 communicate with each other through the openings 113c. The openings 113c are, for example, a plurality of slit-shaped opening 113c extending in parallel as illustrated in FIG. 2. The number of the openings 113c is not particularly limited.

As illustrated in FIG. 4, the first flow path 114 connects the first outlet 111c of the sensor chamber 111 and the second inlet 113a of the treatment chamber 113. As illustrated in FIG. 4, the second flow path 115 connects the second outlet 113b of the treatment chamber 113 and the first inlet 111a of the sensor chamber 111. The first flow path 114 may be connected to the third flow path 117 as illustrated in FIG. 4, or may be an independent flow path without being connected to the third flow path 117.

The filter 116 removes odor substances and moisture (such as water vapor) from the gas in the sensor chamber 111 as the gas passes through the filter 116. For example, activated carbon, silica gel, zeolite, allophane, or the like can be used for the filter 116. As illustrated in FIG. 4, the third flow path 117 connects the first outlet 111c of the sensor chamber 111 and the filter 116. As illustrated in FIG. 4, the fourth flow path 118 connects the filter 116 and the third inlet 11b of the sensor chamber 111.

The first supplying portion 119 circulates a gas between the sensor chamber 111 and the treatment chamber 113 through the first flow path 114 and the second flow path 115. The first supplying portion 119 is a mechanism capable of delivering the gas by using a pump, a fan, or the like, and is disposed in the vicinity of the first inlet 111a in the sensor chamber 111. The first supplying portion 119 may be provided in the middle of the second flow path 115.

The second supplying portion 120 circulates a gas between the sensor chamber 111 and the filter 116 through the third flow path 117 and the fourth flow path 118. The second supplying portion 120 is a mechanism capable of delivering the gas by using a pump, a fan, or the like, and is disposed in the vicinity of the third inlet 111b in the sensor chamber 111. The second supplying portion 120 may be provided in the middle of the fourth flow path 118.

The controlling portion 121 is connected to the sensor module 112, the first supplying portion 119, and the second supplying portion 120, and controls them. The controlling portion 121 can also control a heating body 151 illustrated in FIGS. 19 and 20. The heating body 151 may be a Peltier element. Specifically, the controlling portion 121 vibrates the vibrator of each odor sensor 123 at a predetermined resonance frequency, and acquires an amount of variation in the resonance frequency as the detected value from each odor sensor 123. The controlling portion 121 transmits the acquired detected values of the respective odor sensors 123 to the measuring portion 122. The controlling portion 121 controls the first supplying portion 119 and the second supplying portion 120 to switch the operation state of the odor measuring device 100. This operation state will be described later.

The measuring portion 122 acquires the detected values of the respective odor sensors 123, and determines the odor based on the detected value when the variation in the detected value becomes within a predetermined amount in a predetermined time, for example, when the detected value is stabilized. The measuring portion 122 can measure each odor substance from the detected value of each odor sensor 123 and specify the amount of each odor substance desorbed from the measurement object P. The measuring portion 122 can determine the type and the intensity of the odor desorbed from the measurement object P by using the specified amounts of the odor substances and the reference information stored in the database.

[As to Operation State of Odor Measuring Device]

Figure 7:
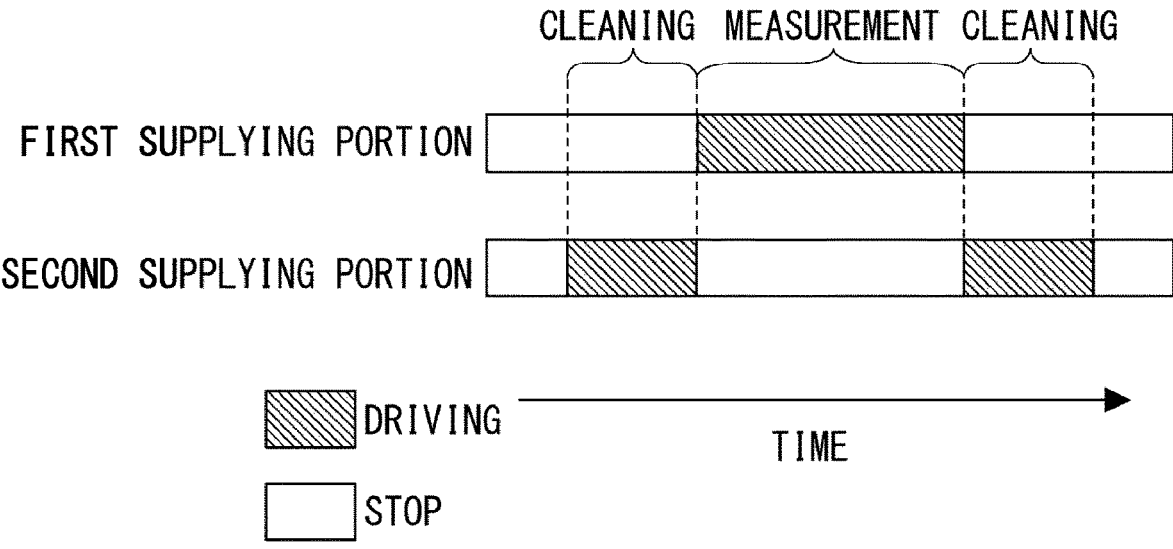
FIG. 7 is a timing chart illustrating an operation state of the odor measuring device.
Figure 8:
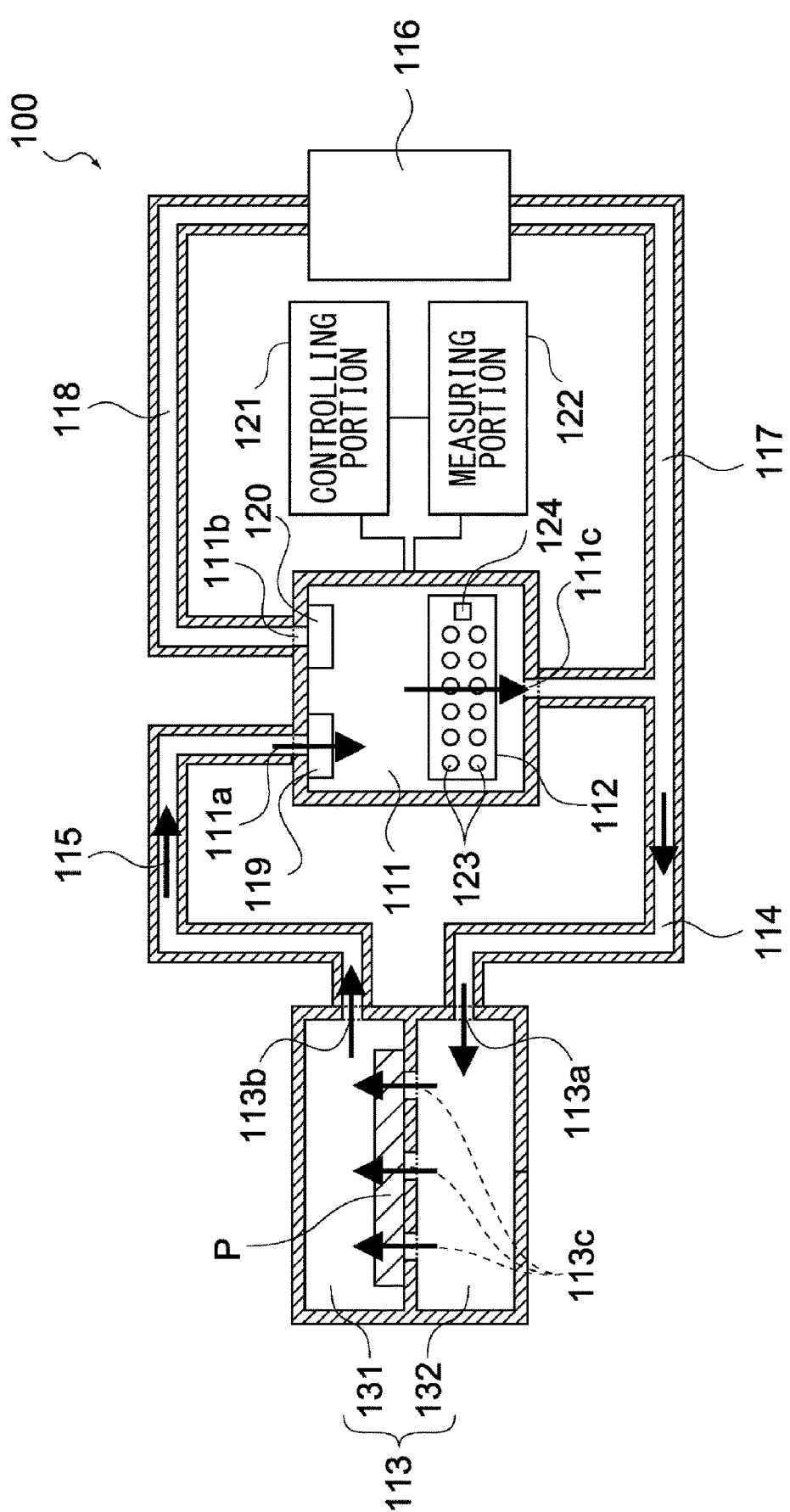
FIG. 8 is a schematic view illustrating a measurement flow of the odor measuring device.
Figure 9:
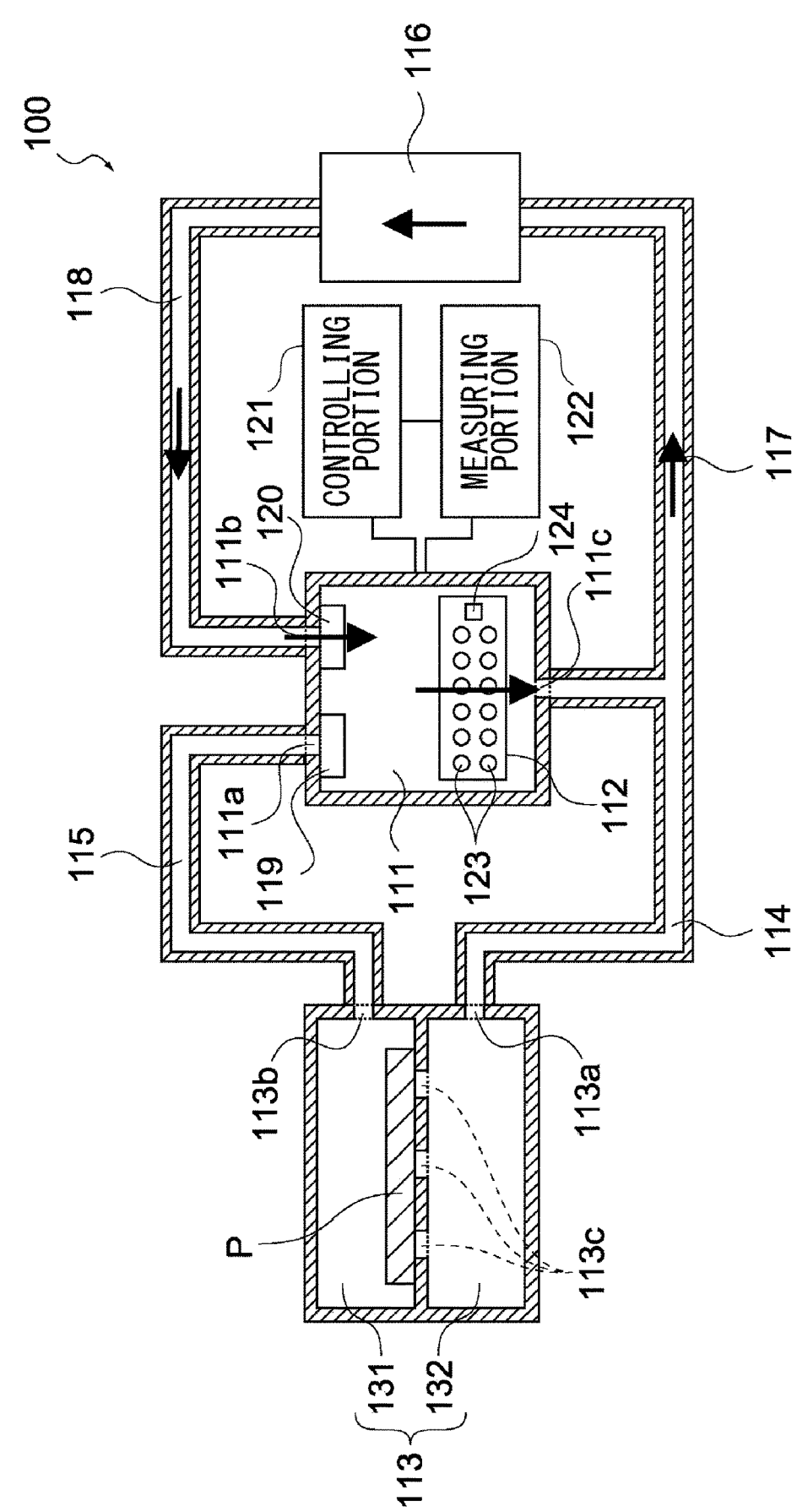
FIG. 9 is a schematic view illustrating a cleaning flow of the odor measuring device.

FIG. 7 is a timing chart illustrating an operation state of the odor measuring device 100, and FIGS. 8 and 9 are schematic views illustrating operations of the odor measuring device 100. As illustrated in FIG. 7, the odor measuring device 100 takes two states, i.e., a "measurement state" and a "cleaning state".

In the measurement state, as illustrated in FIG. 7, the controlling portion 121 drives the first supplying portion 119 and stops driving the second supplying portion 120. As a result, as illustrated by arrows representing gas flow in FIG. 8, the gas flows from the sensor chamber 111 into the first flow path 114 through the first outlet 111c, and from the first flow path 114 into the gas treatment chamber 132 through the second inlet 113a. The gas flows into the desorption treatment chamber 131 through the openings 113c and passes through the measurement object P. Further, the gas flows from the desorption treatment chamber 131 into the second flow path 115 through the second outlet 113b. Further, the gas flows from the second flow path 115 into the sensor chamber 111 through the first inlet 111a. The gas flows from the sensor chamber 111 into the first flow path 114 through the first outlet 111c again, and the above-described flow is repeated. That is, in the measurement state, the gas circulates between the sensor chamber 111 and the treatment chamber 113 through the first flow path 114 and the second flow path 115. Hereinafter, this flow of gas is referred to as a "measurement flow". The measurement object P is a sheet-like body such as a cloth, a mask, a handkerchief, or absorbent cotton, and covers the lower surface 131a including the openings 113c. Therefore, the gas is forced to pass through the measurement object P. When the odor component contained in the measurement object P is a minute amount, the number of circulations illustrated in FIG. 8 is the number of times the odor component reaches the sensitive membrane of the odor sensor 123, and the decrease in sensitivity of the odor sensor 123 due to the circulations is smaller than the decrease in sensitivity of the odor sensor 123 in the case where the odor component does not circulate.

In the cleaning state, as illustrated in FIG. 7, the controlling portion 121 stops the driving of the first supplying portion 119 and drives the second supplying portion 120. As a result, as illustrated by arrows representing gas flow in FIG. 9, the gas flows from the sensor chamber 111 into the third flow path 117 through the first outlet 111c, and flows from the third flow path 117 into the filter 116. The gas passes through the filter 116 and flows into the fourth flow path 118, and then flows into the sensor chamber 111 via the third inlet 111b. The gas flows from the sensor chamber 111 into the third flow path 117 through the first outlet 111c again, and thereafter, the above-described flow is repeated. That is, in the cleaning state, the gas circulates between the sensor chamber 111 and the filter 116 through the third flow path 117 and the fourth flow path 118. Hereinafter, this flow of gas is referred to as a "cleaning flow". By repeating this flow, the sensitive film of the odor sensor 123 and the sensitive film of the humidity sensor are cleaned and reset.

[As to Measuring Process by Odor Measuring Device]

Figure 10:
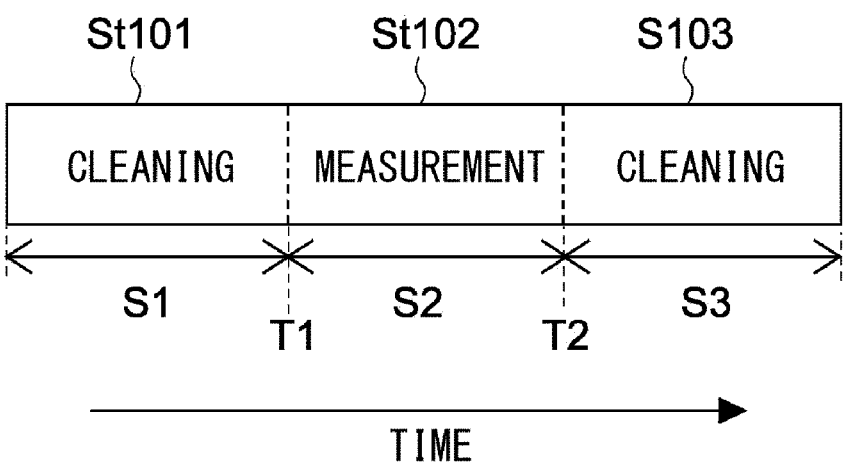
FIG. 10 is a schematic view illustrating an odor measuring process by the odor measuring device.

A odor measuring process by the odor measuring device 100 will be described. First, the lid 102 is opened as illustrated in FIG. 2 or FIG. 6, and the measurement object P is placed in the desorption treatment chamber 131 as illustrated in FIG. 4. Next, the lid 102 is closed to close the desorption treatment chamber 131. Subsequently, the odor measuring process by the odor measuring device 100 is executed. FIG. 10 is a schematic view illustrating the odor measuring process by the odor measuring device 100. As illustrated in FIG. 10, the odor measurement process includes a cleaning step St101, a measurement step St102, and a cleaning step St103.

In the cleaning step St101, the odor measuring device 100 is set in the cleaning state described above, and a cleaning flow as illustrated by the arrows in FIG. 9 is generated. As a result, the odor substance and the moisture adhered to the adsorption film or the like of the odor sensor 123 are desorbed into the gas, and are adsorbed (trapped) by the filter 116 and removed. If a cleaning period of the cleaning step St101 is denoted by S1, the S1 is, for example, 20 minutes. A degree of the cleaning increases as the number of cycles of the flow increases. The direction of the circulation indicated by the arrows in FIG. 9 may be reversed.

Figure 11:
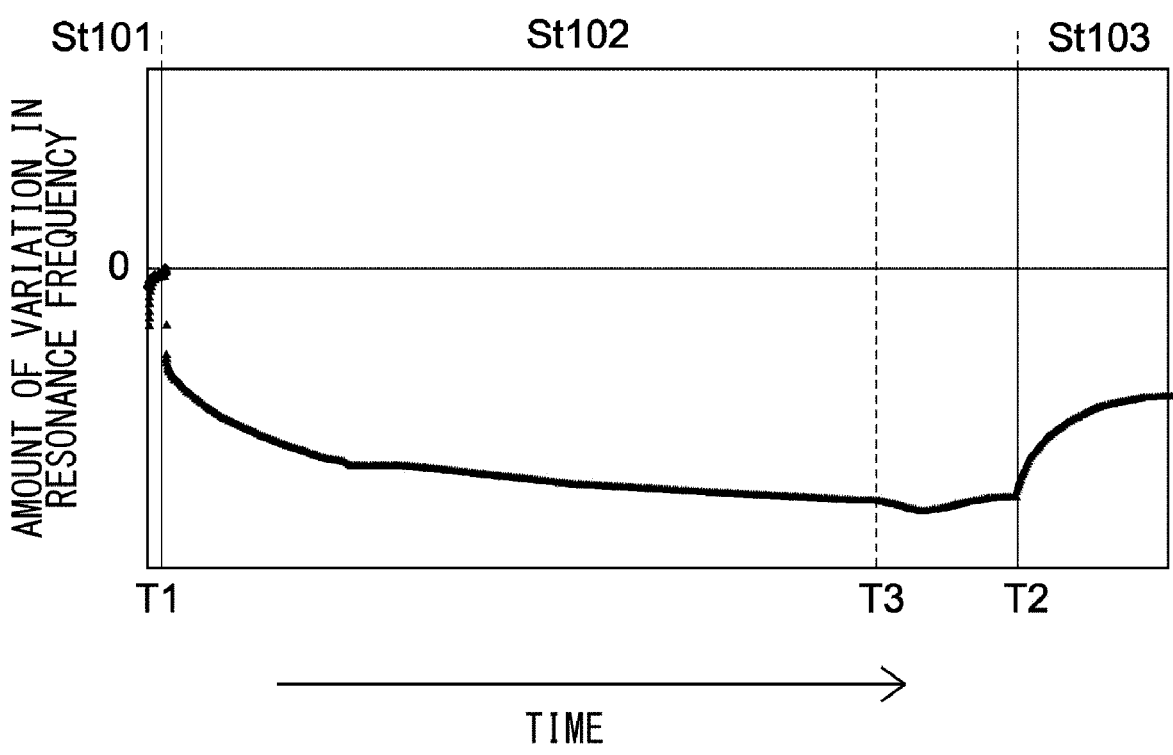
FIG. 11 is a graph illustrating detected values of odor sensors provided in the odor measuring device.

In the measurement step St102, as illustrated by the arrows in FIG. 8, the odor measuring device 100 is brought into the above-described measurement state, and the measurement flow is generated. The odor substance adhered to the measurement object P is desorbed by the measurement flow passing through the measurement object P, and is transported to the sensor chamber 111. The odor substance transported to the sensor chamber 111 is adsorbed on the adsorption film of the odor sensor 123. The odor sensor 123 outputs the detected value to the measuring portion 122. Referring to FIG. 11, when a start time of the measurement step St102 is a time T1, an end time is a time T2, and a measurement period of the measurement step St102 is S2, S2 is a period after the lapse of a time T3 described later. That is, the measurement is performed after the time T3 when the variation has settled.

In the cleaning step St103, the odor measuring device 100 is set in the cleaning state described above, and the cleaning flow indicated by the arrows in FIG. 9 is generated. As a result, the odor substance and the moisture adhered to the adsorption film or the like of the odor sensor 123 are desorbed into the gas, and are adsorbed by the filter 116, whereby the odor of the odor sensor 123 is removed. If the cleaning period of the cleaning step St103 is S3, S3 is, for example, 20 minutes.

After the cleaning step St103, the lid 102 is opened and the measurement object P is taken out. A next measurement object P is placed in the desorption treatment chamber 131, and the odor can be measured in the same manner. The odor measuring process by the odor measuring device 100 is performed as described above. The desorption treatment chamber 131 is detachable, and cleaning can be performed by detaching the chamber after the measurement of the measurement object P. The above-described measurement process may be executed by the user or the controlling portion 121 using the odor measuring device 100.

[As to Odor Measurement by Measuring Portion]

The measuring portion 122 acquires the detected values output from the respective odor sensors 123 as described above. FIG. 11 is a graph illustrating the amount of variation in the resonance frequency, which is a detected value output from one odor sensor 123. As illustrated in FIG. 11, the detected value increases from the start time T1 of the measurement step St102 and gradually stabilizes. The measuring portion 122 specifies a time at which the detected value is stabilized as the time T3. Specifically, the measuring portion 122 specifies, as the time T3, a time at which the variation in the detected value is within a predetermined amount in a predetermined time. The predetermined time is, for example, 60 seconds, and the predetermined amount is, for example, 18 Hz. The measuring portion 122 may specify, as the time T3, a time when the variation in the detected value per second is within the predetermined amount, for example, a time when the variation in the detected value is within ±0.3 Hz/sec. As described above, the expression "the variation in the detected value is within the predetermined amount in the predetermined time" means that the variation of the detected value is stopped, and does not mean the amount of variation in the detected value from the time T1.

The measuring portion 122 measures the odor based on the detected value at the time T3. The measuring portion 122 can specify the amount of the odor substance adsorbed on the adsorption film of the odor sensor 123 from the detected value of each odor sensor 123 at the time T3. In this case, the measuring portion 122 may use a detected value corrected by humidity or temperature. The measuring portion 122 can compare the amount of each of the specified odor substances with the information stored in the database to determine the type and the intensity of the odor desorbed from the measurement object P.

After the time T3 is specified, the measuring portion 122 notifies the controlling portion 121 of the time T3. The controlling portion 121 ends the measurement step St102 illustrated in FIG. 10 at a time after the elapse of the time T3 as the time T2. The controlling portion 121 may set the time T2 to a time after a predetermined time has elapsed from the time T3 or to the same time as the time T3. The controlling portion 121 may set a time after a predetermined time has elapsed from the time T1 as the time T2 regardless of the time T3. The measuring portion 122 can also specify the time T3 after the end of the measurement step St102 and measure the odor based on the detected value at the time T3. The measuring portion 122 may specify, as the time T3, a time at which the variation in the detected value is within the predetermined amount in the predetermined time, or may specify, as the time T3, a time at which the variation in the detected value is within the predetermined amount when the measurement flow indicated by the arrows in FIG. 8 is circulated a plurality of times.

Effects by Odor Measuring Device

Figure 12:
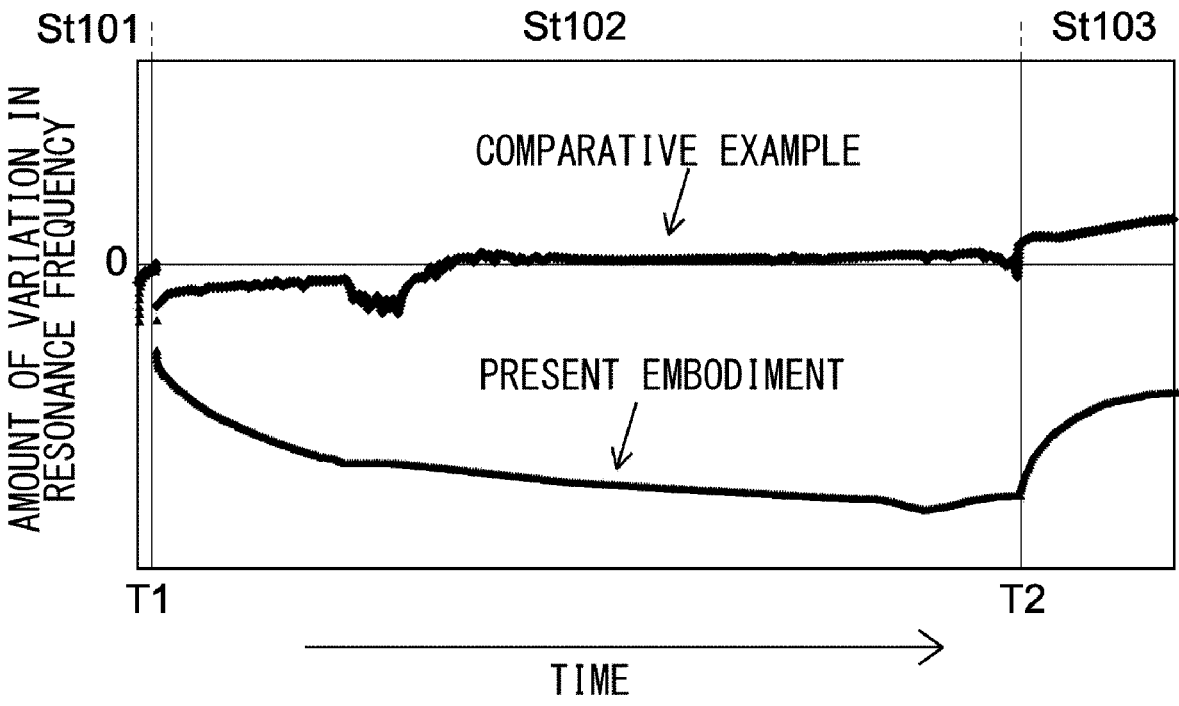
FIG. 12 is a graph illustrating detected values of the odor sensors provided in the odor measuring device and odor sensors provided in an odor measuring device according to a comparative example.

An effect of the odor measuring device 100 will be described in comparison with an odor measuring device according to a comparative example. FIG. 12 is a graph illustrating an amount of variation in the resonance frequency which is the detected value of the odor sensor 123 provided in the odor measuring device 100, and an amount of variation in the resonance frequency of an odor sensor provided in the odor measuring device according to the comparative example. In the figure, the amount of variation in the resonance frequency which is the detected value of the odor sensor 123 provided in the odor measuring device 100 is denoted as "present embodiment", and the amount of variation in the resonance frequency of the odor sensor provided in the odor measuring device according to the comparative example is denoted as "comparative example". The odor measuring device according to the comparative example has a structure in which outside air flows into the treatment chamber storing the measurement object, gas flows from the treatment chamber to the sensor chamber storing the odor sensor, and gas is discharged from the sensor chamber to the outside, and does not have a structure in which the gas circulates between the treatment chamber storing the measurement object, and the sensor chamber.

As illustrated in FIG. 12, in the case of the odor measuring device according to the comparative example, the amount of variation in the resonance frequency is large immediately after the start of measurement, and the amount of variation in the resonance frequency gradually decreases with the elapse of measurement time. This is because the odor substance transported to the odor sensor decreases as the desorption of the odor substance from the measurement object progresses, and the odor substance adsorbed to the odor sensor is gradually desorbed. In this case, it is difficult to determine a time at which the amount of variation in the resonance frequency should be used to specify the amount of the odor substance. A maximum value of the amount of variation in the resonance frequency immediately after the start of the measurement may also change due to the influence of temperature and the like. Thus, in the case of the odor measuring device according to the comparative example, accurate odor measurement may not be performed, and particularly when the amount of the odor substance adhered to the measurement object is small and the concentration of the odor substance is low, it becomes difficult to perform the odor measurement.

In contrast, in the case of the odor measuring device 100 according to the present embodiment, as illustrated in FIG. 12, the amount of variation in the resonance frequency increases with the elapse of the measurement time, and gradually stabilizes. This is because, in the measurement flow indicated by the arrows in FIG. 8, since the gas circulates between the sensor chamber 111 and the treatment chamber 113 and is not discharged to the outside, the odor substance desorbed from the measurement object P is accumulated in the gas, and the concentration of the odor substance in the circulation path becomes uniform. Therefore, the detected value of the odor sensor 123 is stabilized, and the accuracy of odor identification is improved. In particular, even when the amount of the odor substance adhered to the measurement object is small and the concentration of the odor substance is low, the odor substance is not discharged to the outside, and therefore, the odor can be measured with high accuracy. The present embodiment is suitable for a case where the plurality of odor sensors 123 are provided and the types and the intensities of the odors are determined by comparing the patterns of the detected values of the plurality of odor sensors 123 with a learned model of machine learning in which the patterns of the detected values correspond to the types of the odors. This is because, when the types and the intensities of the odors are determined, the types and intensities of the odors can be determined with high accuracy by comparing the patterns of the detected values with the learned model after the concentrations of the odors contained in the gas are stabilized.

[Use of Odor Measuring Device]

The use of the odor measuring device 100 is not particularly limited, but the odor can be measured on a spot using a mask worn by a traveler, a cloth wiped with a baggage, or the like at a security inspection of an airport, a port, or the like. In other words, the device can be used as a capturing type odor measuring device. Since the odor measuring device 100 is suitable for measuring odor at the low concentration as described above, the odor measuring device 100 can be suitably used for such a use. For example, in the case of detecting a banned drug, even if the banned drug is present in the cloth in an extremely small amount, the banned drug can be detected by the odor sensor 123 if the circulation illustrated in FIG. 8 is performed for a long time. The presence or absence of the banned drug is more important than the measurement of its concentration. In the circulation illustrated in FIG. 8, the gas containing the drug passes through the sensitive membrane of the odor sensor 123 many times, so that the detection capability of the odor sensor 123 is increased.

[As to Pressing Structure]

Figure 13:
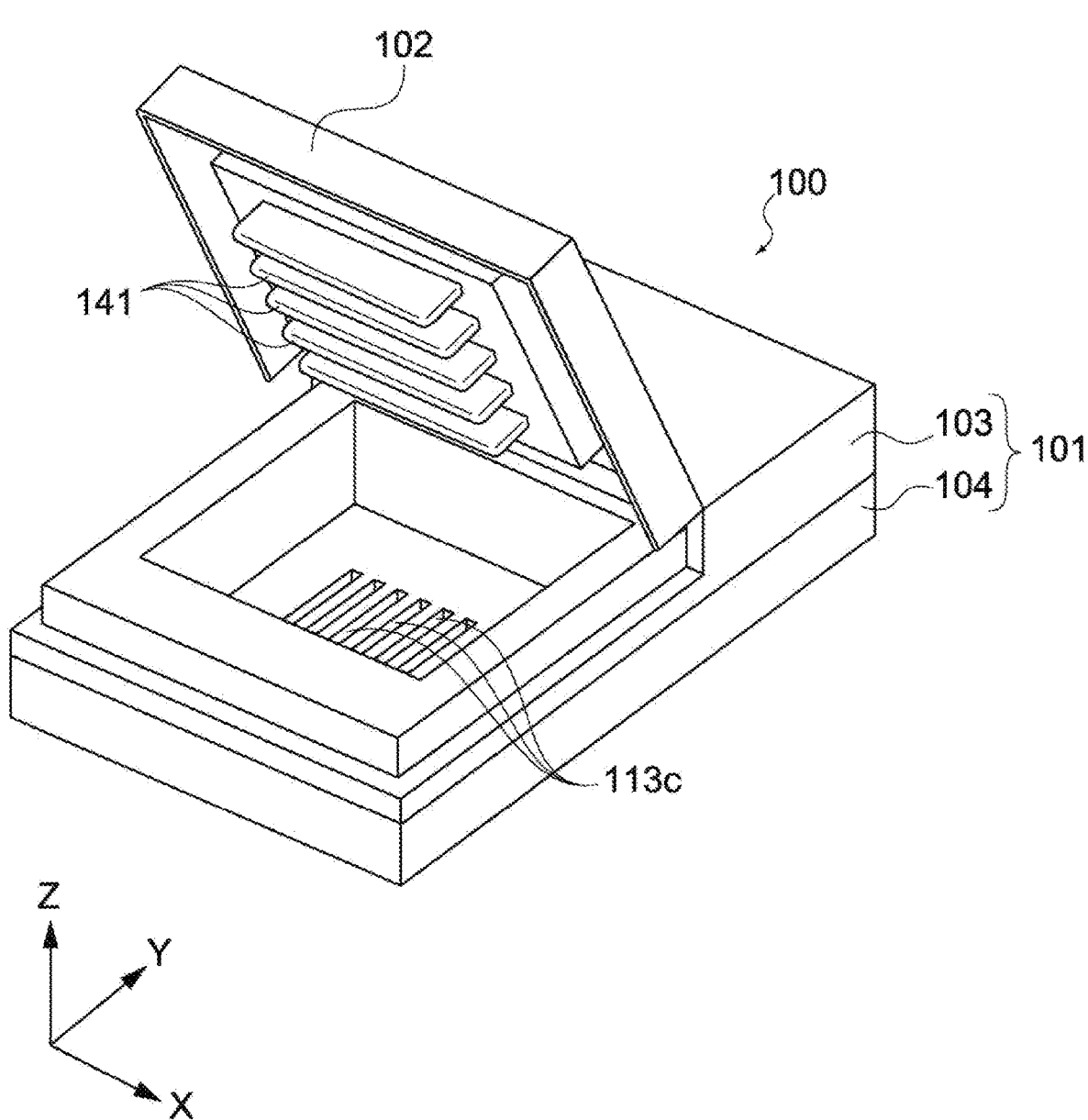
FIG. 13 is a perspective view of an odor measuring device including a pressing portion according to the embodiment.
Figure 14:
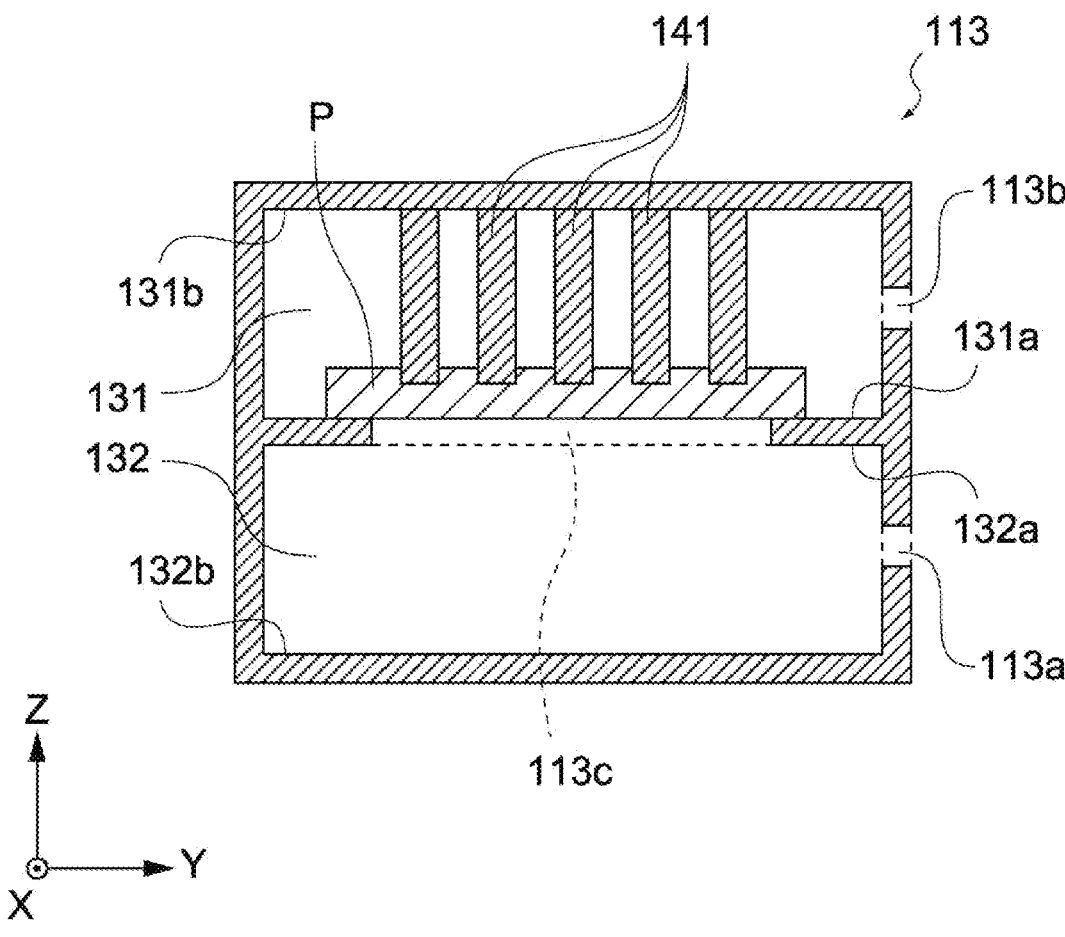
FIG. 14 is a schematic view of a treatment chamber provided in the odor measuring device.

The odor measuring device 100 may have a pressing structure that presses the measurement object P. FIG. 13 is a perspective view of the odor measuring device 100 having the pressing structure, and FIG. 14 is a schematic view of the treatment chamber 113 of the odor measuring device 100 having the pressing structure. As illustrated in these figures, the desorption treatment chamber 131 may include a pressing portion 141 protruding from the upper surface 131b toward the lower surface 131a. When the desorption treatment chamber 131 is closed by the lid 102, the pressing portion 141 presses the measurement object P together with the lower surface 131a as illustrated in FIG. 14. The lower surface 131a is provided with the opening 113c as described above, and in the measurement flow illustrated by the arrows in FIG. 8, the gas passes through the measurement object P from the gas treatment chamber 132 through the opening 113c.

At this time, if the measurement object P is bent or lifted, an air resistance in this space is small, and therefore the gas is discharged from the desorption treatment chamber 131 without passing through the measurement object P, and the odor substance may be difficult to be desorbed from the measurement object P. Here, the pressing portion 141 presses the measurement object P against the lower surface 131a, so that the bending and the lifting of the measurement object P are eliminated, and the odor substance can be surely desorbed from the measurement object P.

Figure 15:
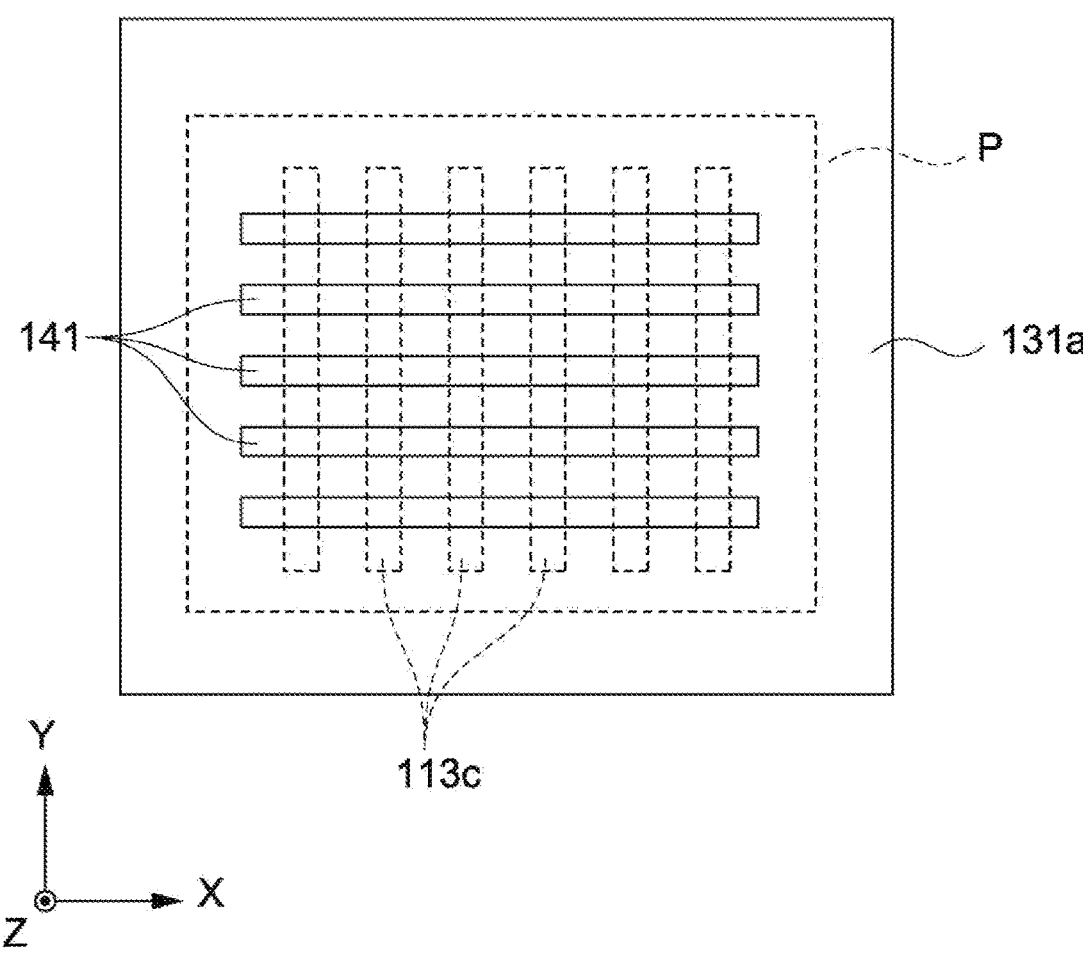
FIG. 15 is a plan view of the treatment chamber provided in the odor measuring device.

The shape of the pressing portion 141 is not particularly limited, but the following shape is preferable. FIG. 15 is a plan view illustrating the shape of the pressing portion 141. As illustrated in FIGS. 13 and 15, the pressing portion 141 is a wall-shaped body (plate-shaped body) extending downward from the upper surface 131b, and may be formed to extend in an X direction which is a direction perpendicular to an extending direction of the openings 113c which is a Y direction. With this shape, the openings 113c and the pressing portion 141 are arranged in a lattice pattern, and the measurement object P can be pressed reliably. This is because, if the extending direction of the openings 113c and the extending direction of the wall-shaped body are coincident with each other, the wall-shaped body or the measurement object may block the opening.

Figure 16:
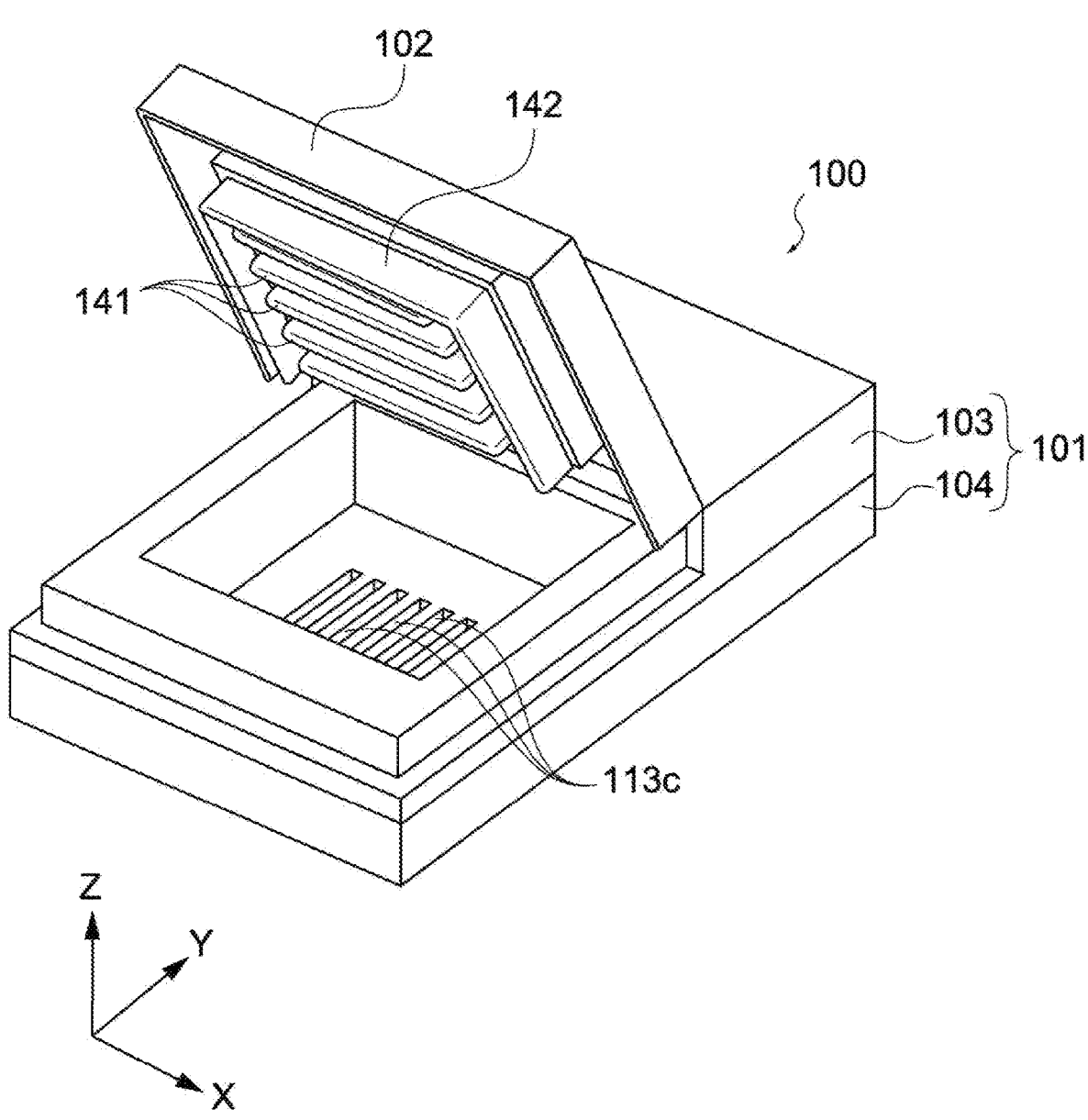
FIG. 16 is a perspective view of an odor measuring device including a pressing portion and a side wall portion according to the embodiment.
Figure 17:
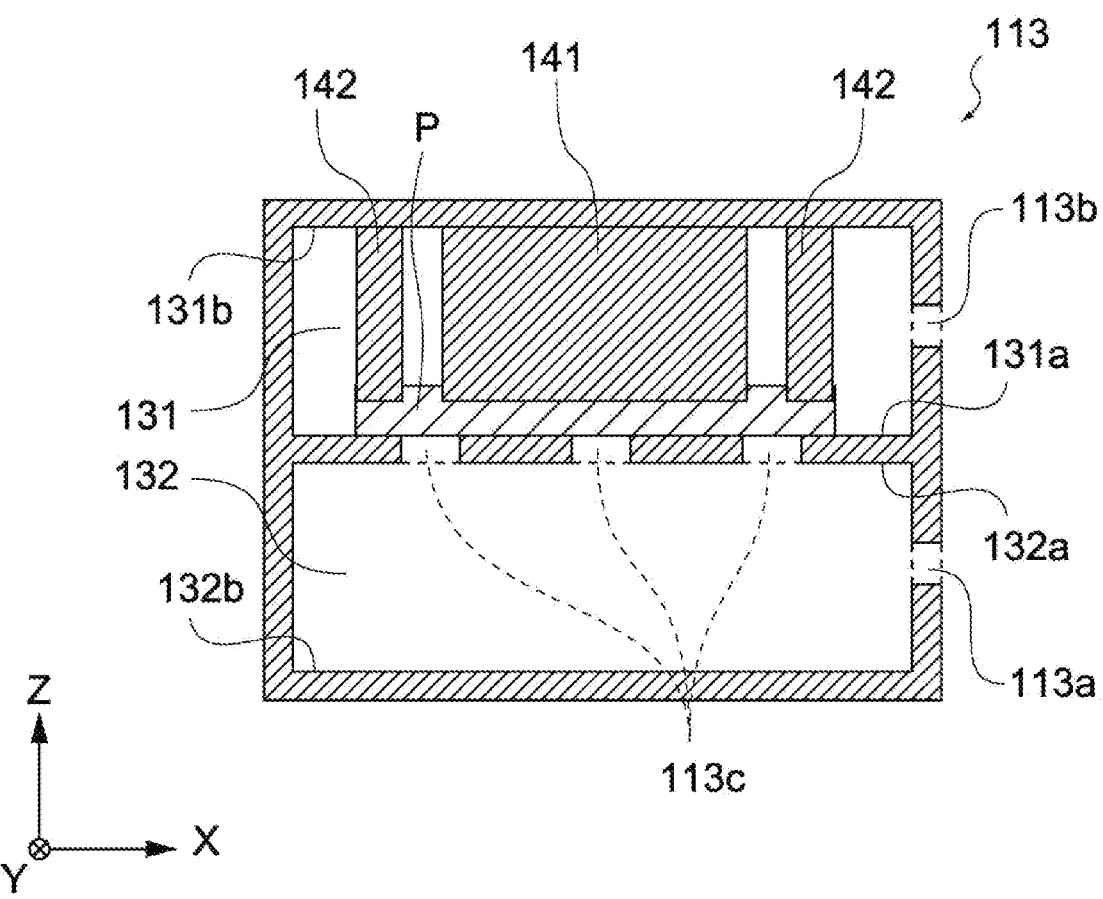
FIG. 17 is a schematic view of a treatment chamber provided in the odor measuring device.
Figure 18:
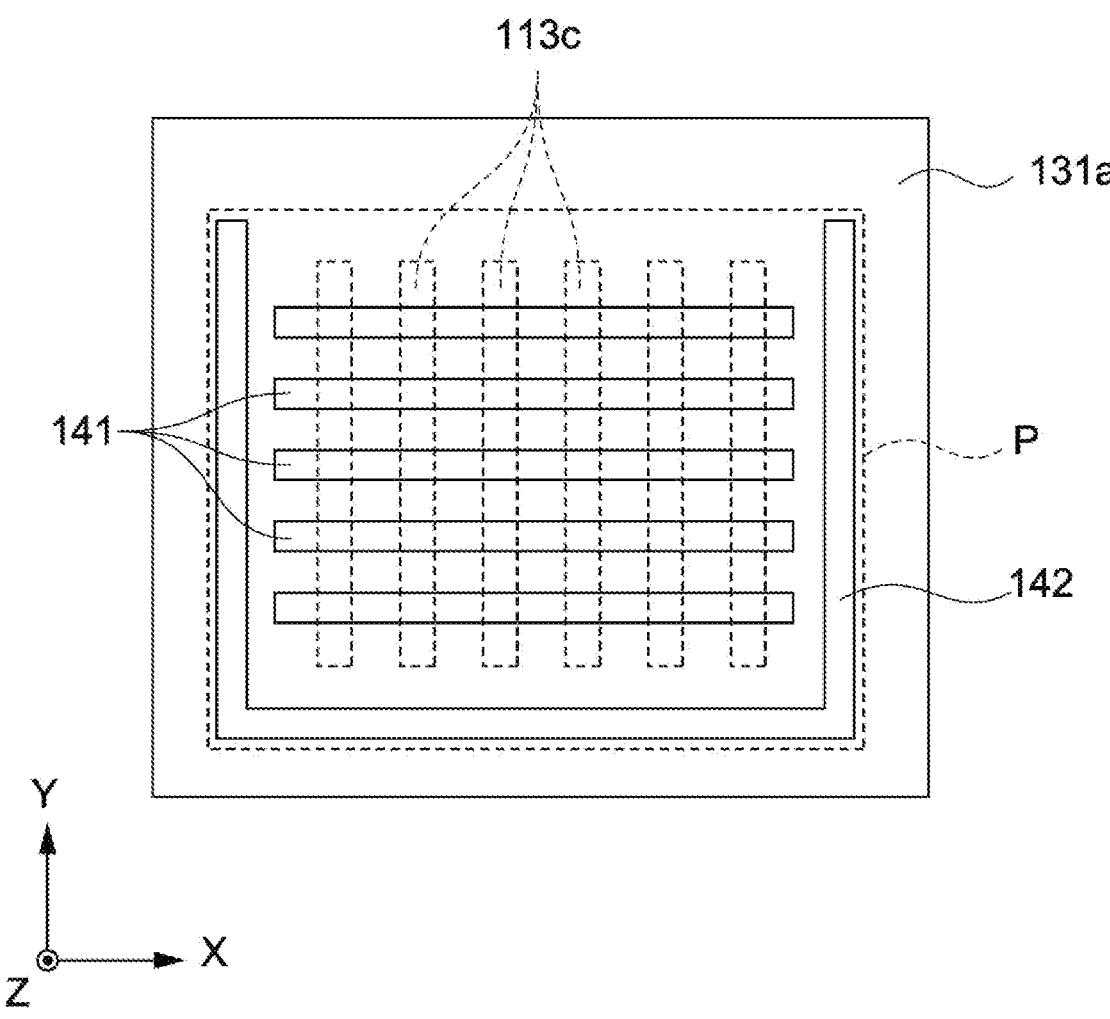
FIG. 18 is a plan view of the treatment chamber provided in the odor measuring device.

The desorption treatment chamber 131 may further include a side wall portion. FIG. 16 is a perspective view of the odor measuring device 100 including the pressing portion 141 and a side wall portion 142, and FIG. 17 is a schematic view of the treatment chamber 113 of the odor measuring device 100 including the pressing portion 141 and the side wall portion 142. FIG. 18 is a plan view illustrating the shapes of the pressing portion 141 and the side wall portion 142. As illustrated in these drawings, the side wall portion 142 has a wall shape that projects from the upper surface 131b toward the lower surface 131a and surrounds three sides of the pressing portion 141. With this shape, the side wall portion 142 can sandwich a peripheral edge portion of the measurement object P together with the lower surface 131a, and can reliably press the entire measurement object P. In this way, the bending and lifting of the measurement object P can be further suppressed, and the odor substance can be easily desorbed from the measurement object P. Further, since the gas is prevented from escaping to the side without directly hitting the measurement object P, the odor substance can be more easily desorbed from the measurement object P. The desorption treatment chamber 131 may not include the pressing portion 141 but may include only the side wall portion 142.

[As to Heating Body]

Figure 19:
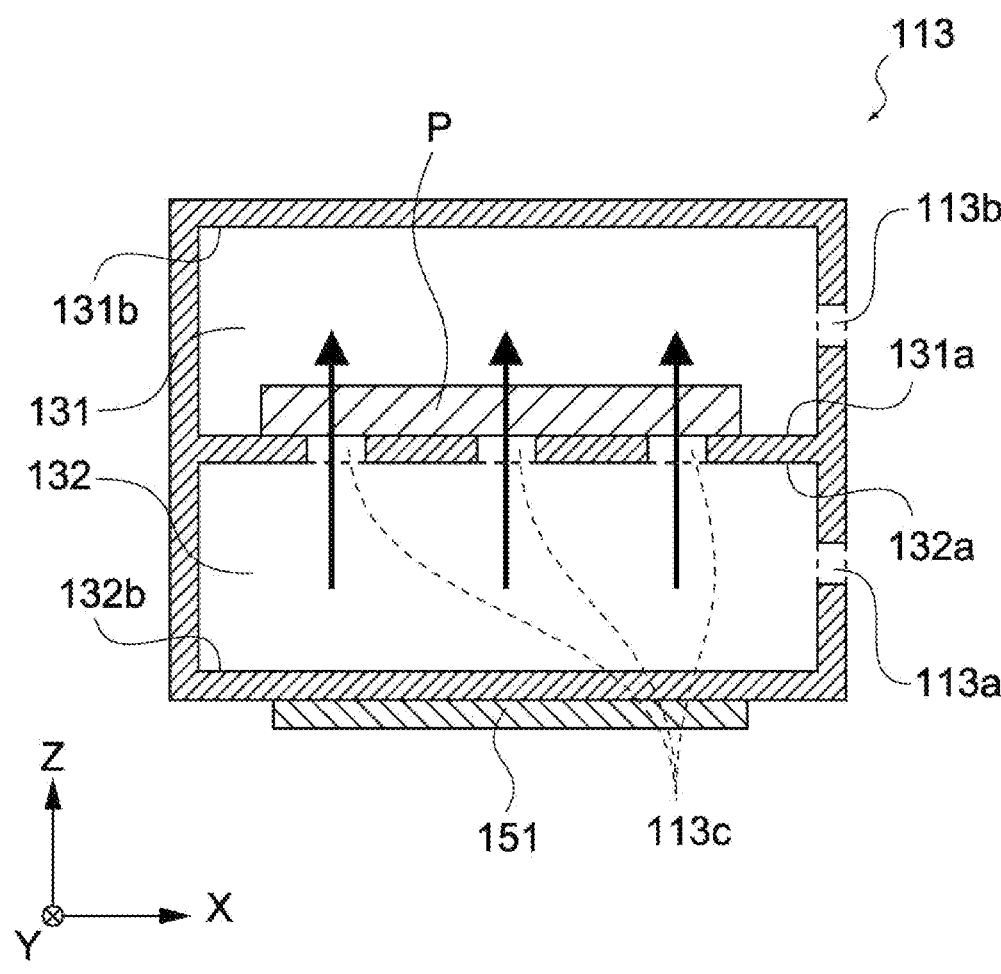
FIG. 19 is a schematic view of a treatment chamber provided in an odor measuring device including a heating body according to the embodiment.

The odor measuring device 100 may include a heating body that heats the measurement object. FIG. 19 is a schematic view of the treatment chamber 113 in which a heating body 151 is provided. As illustrated in FIG. 2, the heating body 151 is provided on the back surface of the lower surface 132b outside the gas treatment chamber 132. By causing the heating body 151 to generate heat during the measurement flow illustrated in FIG. 8, the gas in the gas treatment chamber 132 is heated, and as a result, the temperature of the measurement target P is raised, and the desorption of the odor substance from the measurement object P can be promoted, and the odor substance adhered to the flow path and the inner wall of the treatment chamber 113 can be desorbed. Further, by disposing the heating body 151 under or below the measurement object P, an ascending air current indicated by arrows in the drawing is generated, and the gas can be efficiently applied to the measurement object P. As the heating body, a sheet-shaped Peltier element may be employed.

Figure 20:
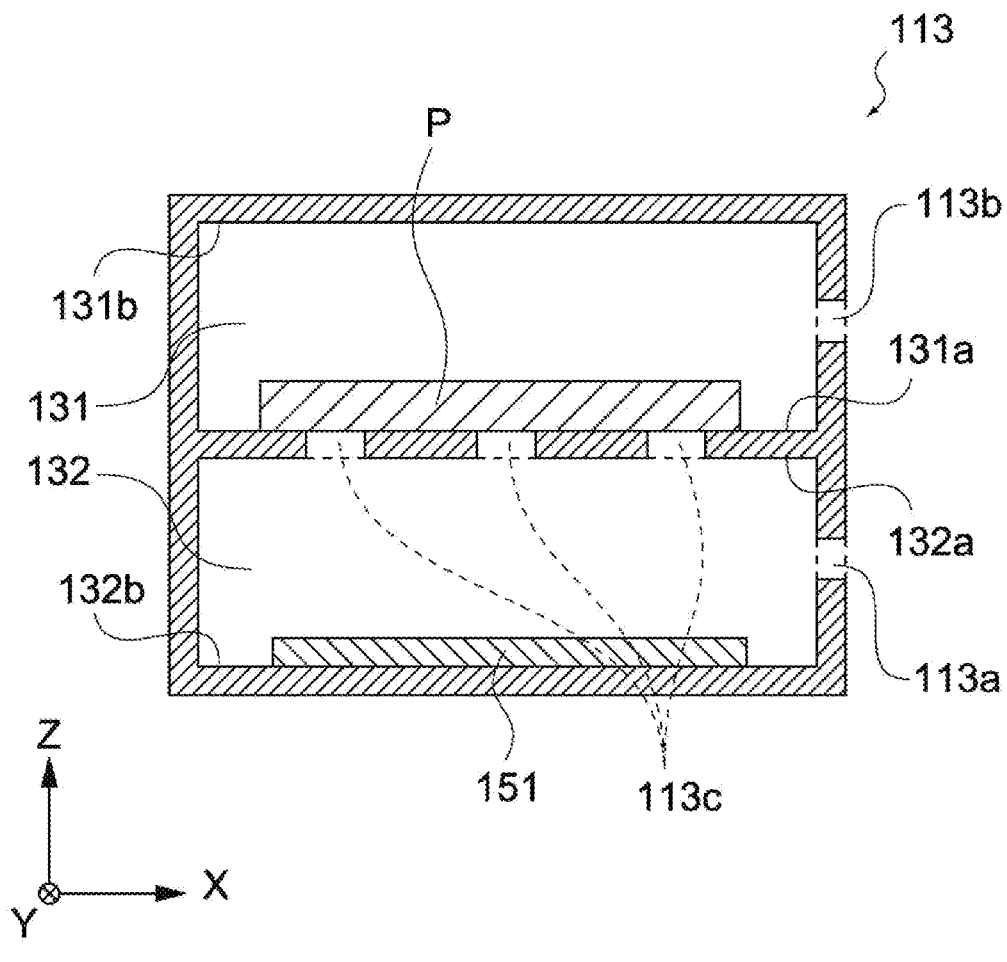
FIG. 20 is a schematic view illustrating another arrangement of the heating body in the treatment chamber provided in the odor measuring device.
Figure 21:
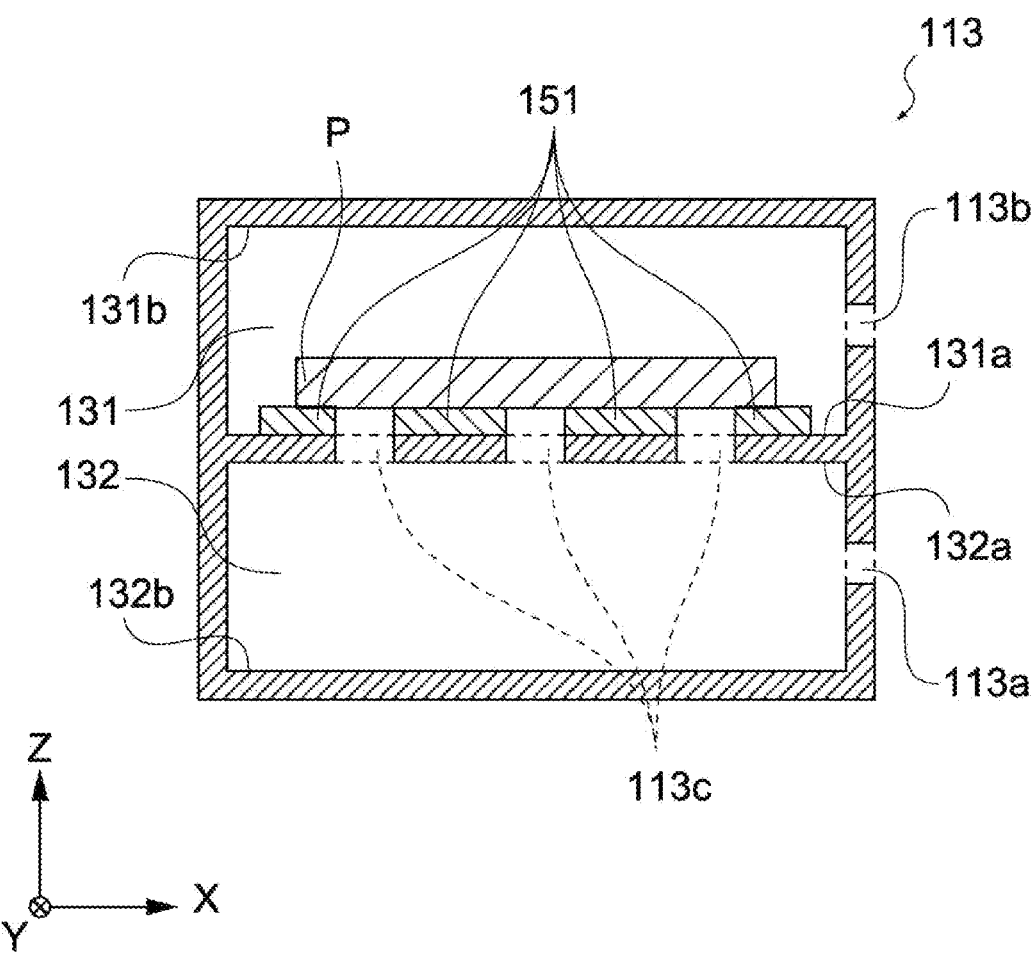
FIG. 21 is a schematic view illustrating another arrangement of the heating body in the treatment chamber provided in the odor measuring device.
Figure 22:
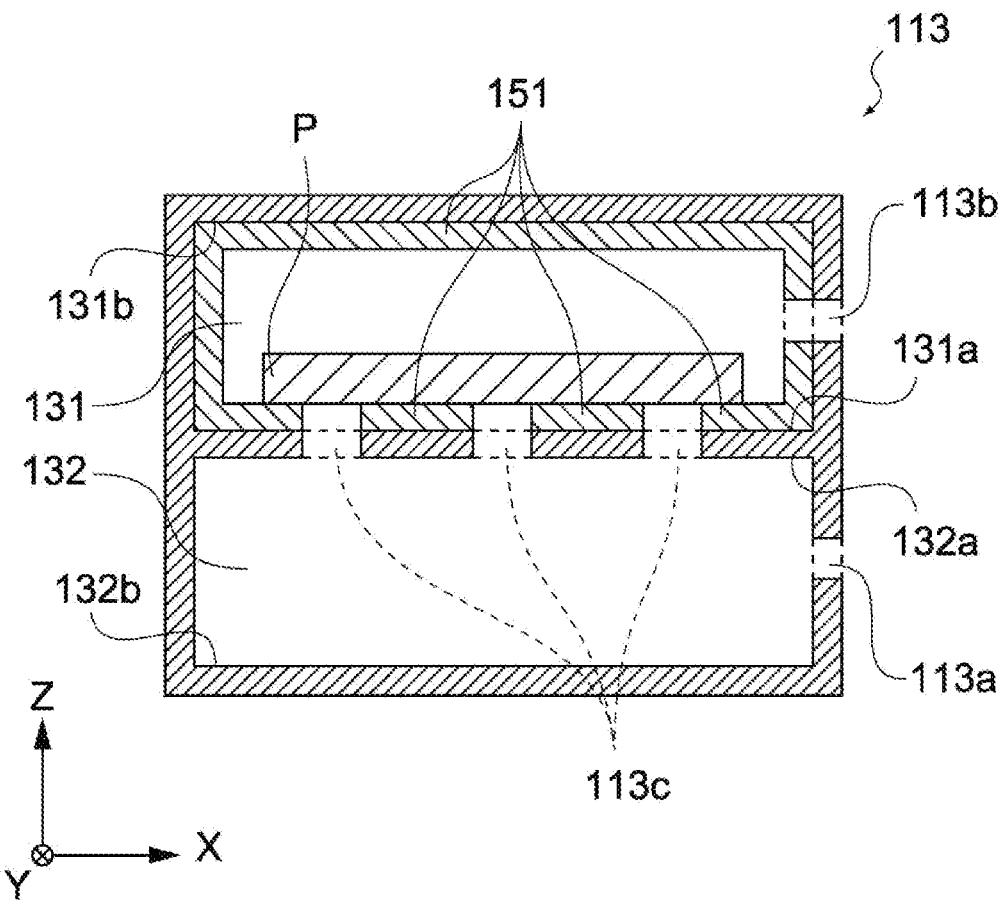
FIG. 22 is a schematic view illustrating another arrangement of the heating body in the treatment chamber provided in the odor measuring device.

The arrangement of the heating body 151 is not limited to the above-described arrangement. FIGS. 20 to 22 are schematic views illustrating another arrangement of the heating body 151. As illustrated in FIG. 20, the heating body 151 may be disposed on the lower surface 132b which is the interior of the gas treatment chamber 132. As illustrated in FIG. 21, the heating body 151 may be disposed around the openings 113c on the lower surface 131a of the desorption treatment chamber 131. In this configuration, since the heating body 151 and the measurement object P are close to each other, the measurement object P can be efficiently heated. The heating body 151 may be disposed around the openings 113c on the upper surface 132a of the gas treatment chamber 132. If the heating body is a sheet, slits may be provided in the sheet, and the slits and the openings 113c may be aligned with each other.

Further, as illustrated in FIG. 22, the heating body 151 may be disposed on the entire inner wall of the desorption treatment chamber 131. This configuration can suppress the adhesion of the odor substance to the inner wall of the desorption treatment chamber 131, and is particularly effective in the case where the odor substance has the low concentration. In addition, the heating body 151 can be disposed outside or in at least one of the desorption treatment chamber 131 and the gas treatment chamber 132, or in both the desorption treatment chamber 131 and the gas treatment chamber 132. The odor measuring device 100 may include the pressing portion 141 and the side wall portion 142 as described above, in addition to the heating body 151.

[As to Liquid Measurement Object]

Figure 23:
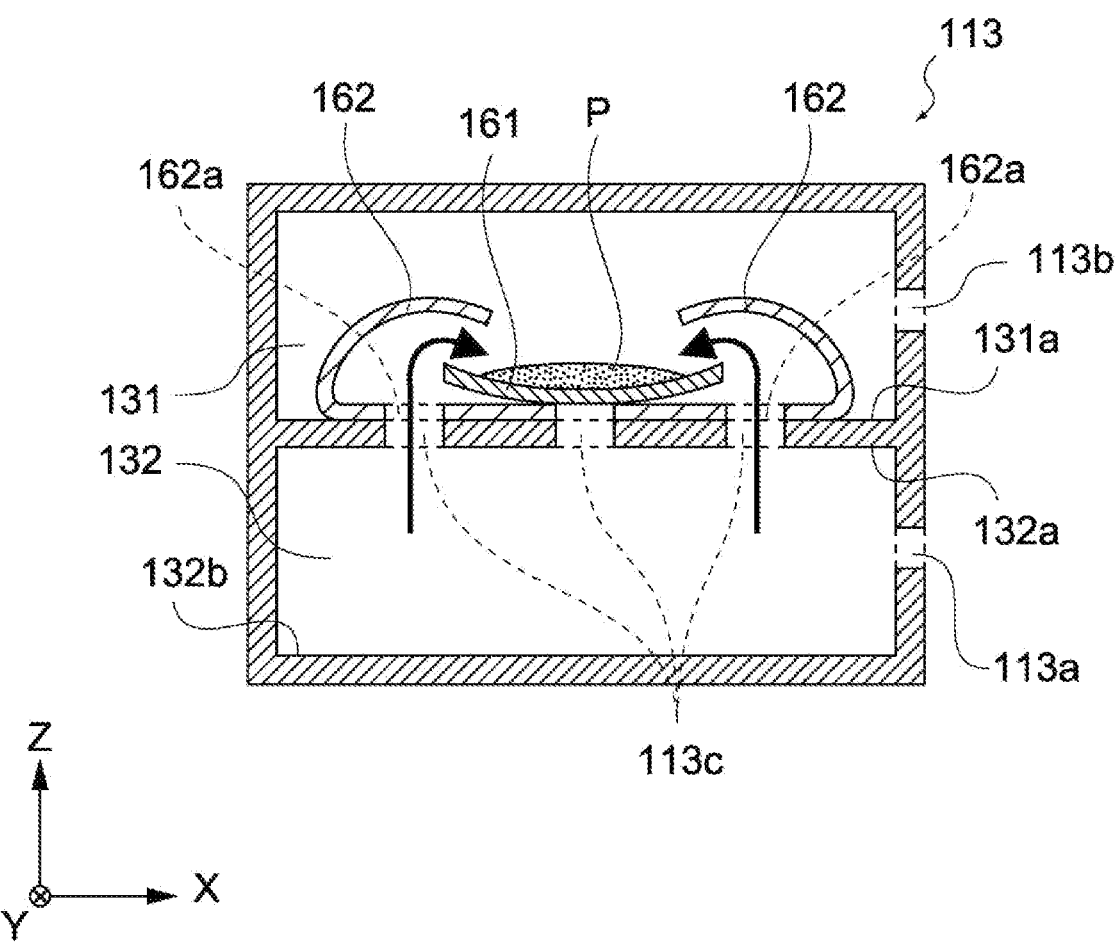
FIG. 23 is a schematic view illustrating the treatment chamber storing a liquid measurement object in the odor measuring device according to the embodiment.

The odor measuring device 100 can measure the odor of a liquid measurement object. FIG. 23 is a schematic view illustrating a method of measuring a liquid measurement object P. As illustrated in FIG. 23, the liquid measurement object P is placed in the pan 161 and then the pan 161 is placed in a case 162. The case 162 has openings 162a communicating with the openings 113c, and has a curved shape for guiding the gas flowing in from the openings 162a to the measurement object P as illustrated by arrows in the figure. This allows the gas flowing in from the openings 162a to efficiently hit the measurement object P, thereby promoting the vaporization of the measurement object P.

Modifications

Figure 24:
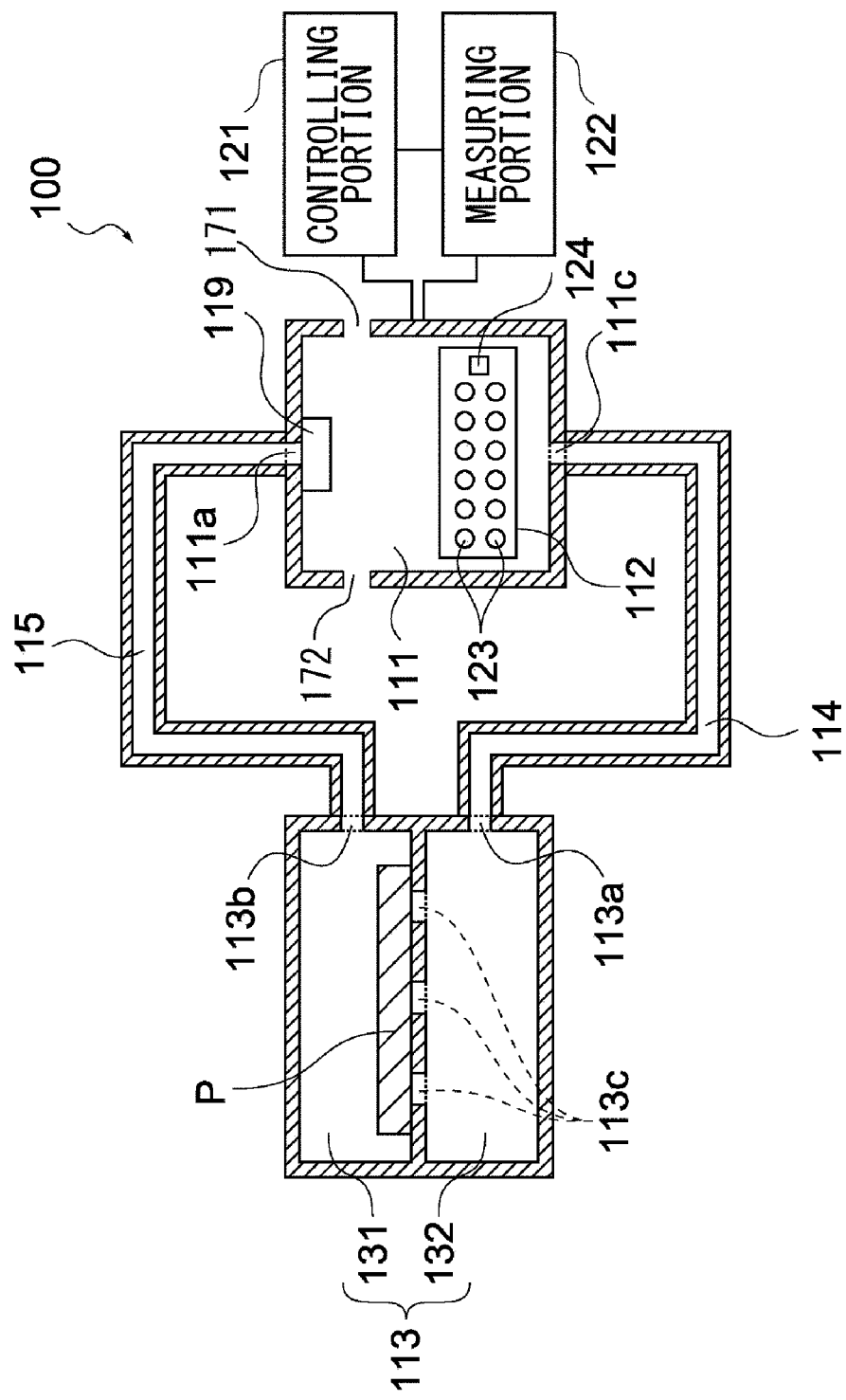
FIG. 24 is a schematic view of an odor measuring device according to a modification.
Figure 25:
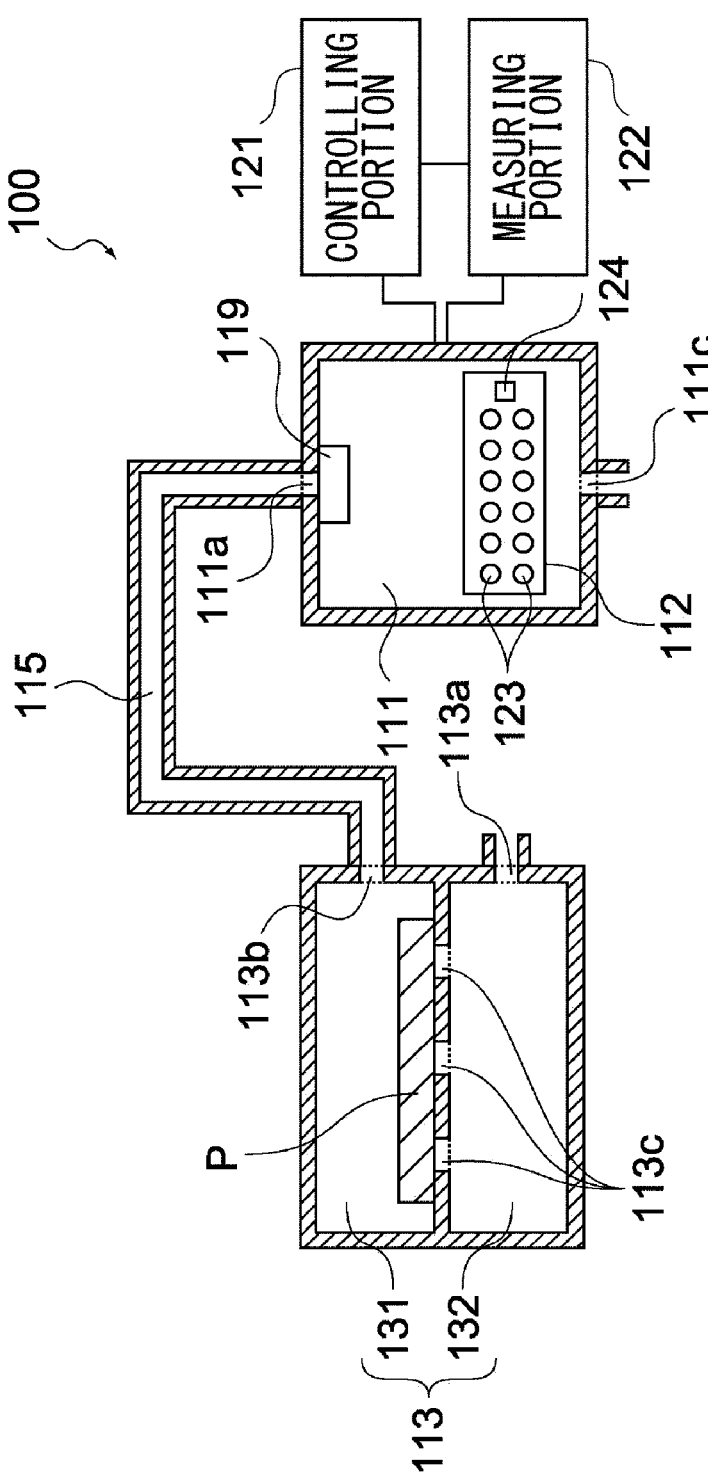
FIG. 25 is a schematic view of an odor measuring device according to a modification.
Figure 26:
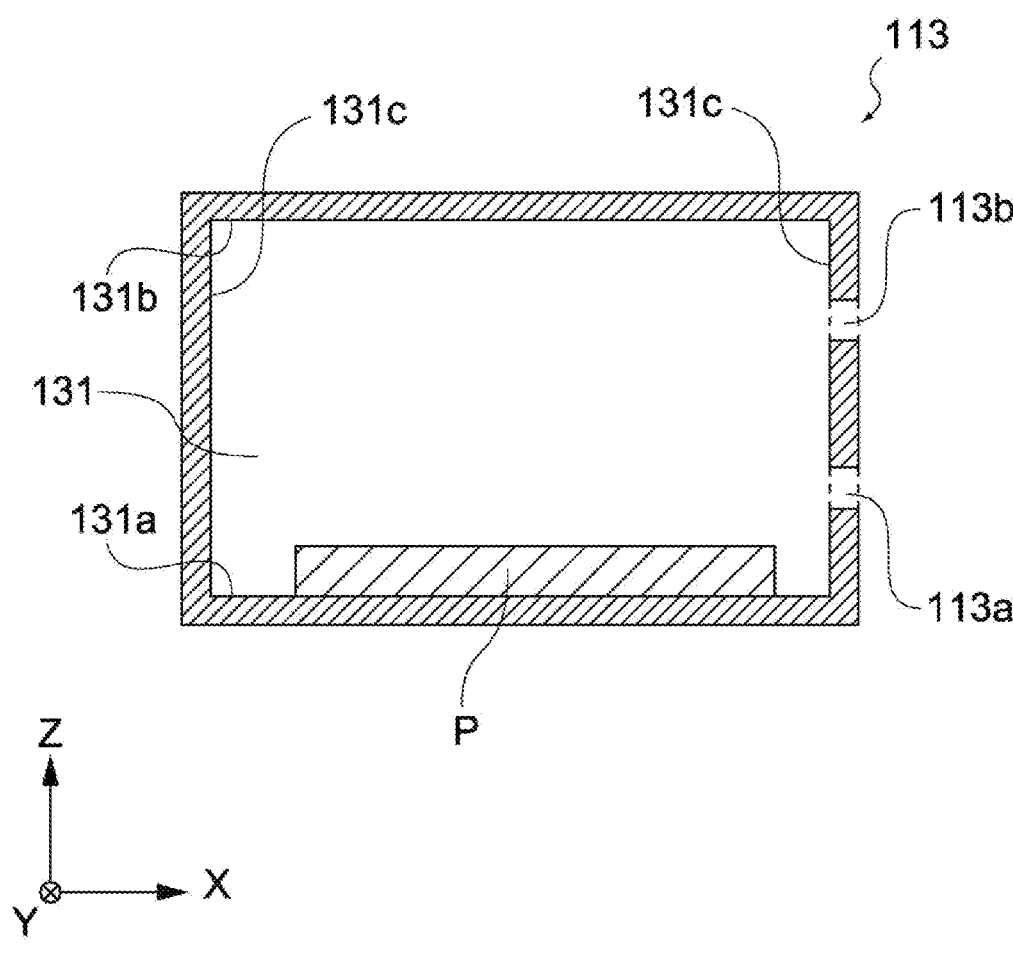
FIG. 26 is a schematic view of a treatment chamber provided in an odor measuring device according to a modification.

Modifications of the odor measuring device 100 will be described. FIGS. 24 to 26 are schematic views illustrating the modifications of the odor measuring device 100. As illustrated in FIG. 24, the odor measuring device 100 may not include the filter 116, the third flow path 117, and the fourth flow path 118. Instead, the odor measuring device 100 includes an opening 171 through which the cleaning gas flows and an outlet 172 through which the cleaning gas is discharged. In this configuration, the cleaning can be performed by flowing the cleaning gas into the sensor chamber 111 from the opening 171, cleaning the odor sensor 123, and then discharging a gas passed through the odor sensor 123 from the outlet 172. As the cleaning gas, an odorless gas may be allowed to flow in, or a gas that is taken in from the outside air and from which the odor substance is removed by a filter may be allowed to flow in. In this structure, a part or all of the pressing portion 141, the side wall portion 142, and the heating body 151 may be provided.

Further, as illustrated in FIG. 25, the odor measuring device 100 may not include the first flow path 114. In this configuration, the circulating measurement flow illustrated in FIG. 8 is not generated, but the driving of the first supplying portion 119 forms a measurement flow in which outside air flows into the treatment chamber 113 from the second inlet 113a, flows into the sensor chamber 111 through the second flow path 115, and is discharged from the first outlet 111c. By this measurement flow, the odor substance desorbed from the measurement object P is supplied to the odor sensor 123 and measured. In this structure, a part or all of the pressing portion 141, the side wall portion 142, and the heating body 151 may be provided.

In the above description, the treatment chamber 113 has two chambers, i.e., the desorption treatment chamber 131 and the gas treatment chamber 132. FIG. 26 is a schematic view illustrating the treatment chamber 113 of the odor measuring device 100 according to the modification. As illustrated in FIG. 26, the treatment chamber 113 may include only the desorption treatment chamber 131. In this configuration, since the gas does not pass through the measurement object P, the desorption rate of the odor substance from the measurement object P is small, but since the odor substance is not discharged during the measurement in the odor measuring device 100, the odor substance can be measured by performing the measurement for a predetermined time. In this configuration, the heating body 151 can be provided inside or outside the desorption treatment chamber 131.

Although the embodiments of the present invention have been described in detail, it is to be understood that the various change, substitutions, and alterations could be made hereto without departing from the spirit and scope of the invention.

What is claimed is:

1. An odor measuring device comprising:
a sensor chamber that stores a sensor detecting an odor substance and has a first inlet and a first outlet;
a treatment chamber that stores a measurement object and has a second inlet and a second outlet;
a first flow path that connects the first outlet and the second inlet;
a second flow path that connects the second outlet and the first inlet;
a supplier that circulates a gas between the sensor chamber and the treatment chamber through the first flow path and the second flow path; and
a measurer that acquires a detected value from the sensor and measures an odor based on the detected value.

2. The odor measuring device according to claim 1, wherein
the treatment chamber includes a desorption treatment chamber having the second outlet and storing the measurement object, and a gas treatment chamber having the second inlet and communicating with the desorption treatment chamber through an opening.

3. The odor measuring device according to claim 2, wherein
the desorption treatment chamber has a lower surface provided with the opening and an upper surface facing the lower surface, and includes a pressing portion projecting from the upper surface toward the lower surface and pressing the measurement object together with the lower surface.

4. The odor measuring device according to claim 3, wherein
the desorption treatment chamber further includes a side wall portion projecting from the upper surface toward the lower surface and pressing a peripheral edge portion of the measurement object together with the lower surface.

5. The odor measuring device according to claim 2, further comprising:
a heating body heating the measurement object.

6. The odor measuring device according to claim 5, wherein
the heating body is disposed around the opening.

7. The odor measuring device according to claim 5, wherein
the heating body is disposed in the gas treatment chamber.

8. The odor measuring device according to claim 5, wherein
the heating element is disposed in the desorption treatment chamber.

9. The odor measuring device according to claim 1, wherein
the sensor includes a plurality of odor sensors having different detection sensitivities according to odor substances, and
the measurer determines odors based on detected values of the plurality of odor sensors.

10. The odor measuring device according to claim 1, wherein the treatment chamber includes:

a desorption treatment chamber that has a space defined by an upper surface, a lower surface, and side surfaces connecting the upper surface and the lower surface, and is capable of disposing a sheet-shaped body on the lower surface;

a plurality of openings that are provided on the lower surface of the desorption treatment chamber and are covered with the sheet-shaped body;

a plurality of wall-shaped bodies that are provided from the upper surface toward the lower surface and press the sheet-shaped body; and an outlet that transports a gas passed through the opening and the sheet-shaped body to an outside.

11. The odor measuring device according to claim 1, wherein the treatment chamber includes:

a desorption treatment chamber that has a space defined by an upper surface, a lower surface, and side surfaces connecting the upper surface and the lower surface, and is capable of disposing a sheet-shaped body on the lower surface;

a plurality of slit-shaped openings that are provided on the lower surface of the desorption treatment chamber, are covered with the sheet-shaped body, and extend in parallel, a plurality of wall-shaped bodies that are provided from the upper surface toward the lower surface, press the sheet-shaped body, and intersect the openings; and an outlet that transports a gas passed through the openings and the sheet-shaped body to an outside.

12. The odor measuring device according to claim 1, wherein the treatment chamber includes:

a desorption treatment chamber that has a space defined by an upper surface, a lower surface, and side surfaces connecting the upper surface and the lower surface, and is capable of disposing a sheet-shaped body on the lower surface;

a plurality of slit-shaped openings that are provided on the lower surface of the desorption treatment chamber, are covered with the sheet-shaped body, and extend in parallel, a plurality of wall-shaped bodies that are provided from the upper surface toward the lower surface, press the sheet-shaped body, and intersect the openings;

a sheet-shaped heating body that is provided on a back side of the openings or on a front side of the openings; and an outlet that transports a gas passed through the openings and the sheet-shaped body to an outside.

13. The odor measuring device according to claim 12, wherein the heating body is composed of a Peltier element.

14. An odor measuring device comprising:

a sensor chamber that stores a sensor detecting an odor substance and has a first inlet and a first outlet;

a treatment chamber that includes a desorption treatment chamber having a second outlet and storing a measurement object, and a gas treatment chamber having a second inlet and communicating with the desorption treatment chamber through an opening, wherein the desorption treatment chamber has a lower surface provided with the opening and an upper surface facing the lower surface, and includes a pressing portion projecting from the upper surface toward the lower surface and pressing the measurement object together with the lower surface;

a flow path that connects the second outlet and the first inlet;

a supplier that delivers a gas in the treatment chamber to the sensor chamber through the flow path; and a measurer that acquires a detected value from the sensor and measures an odor based on the detected value.

15. An odor measuring method executed by an odor measuring device that includes a sensor chamber that stores a sensor detecting an odor substance and has a first inlet and a first outlet, a treatment chamber that has a second inlet and a second outlet, a first flow path that connects the first outlet and the second inlet, a second flow path that connects the second outlet and the first inlet, and a supplier that circulates a gas between the sensor chamber and the treatment chamber through the first flow path and the second flow path, the odor measuring method comprising:

storing a measurement object in the treatment chamber;

circulating the gas between the sensor chamber and the treatment chamber by the supplier; and measuring an odor based on a detected value acquired from the sensor.

* * * * *